(12) United States Patent
Pugsley

(10) Patent No.: US 11,901,059 B2
(45) Date of Patent: Feb. 13, 2024

(54) SYSTEM AND DEVICE FOR REMOTE MONITORING

(71) Applicant: Thesus Medical Products Group, Inc., Fairfax, VA (US)

(72) Inventor: Matthew Pugsley, Fairfax, VA (US)

(73) Assignee: THESUS MEDICAL PRODUCTS GROUP, INC., Fairfax, VA (US)

(*) Notice: Subject to any disclaimer, the term of this patent is extended or adjusted under 35 U.S.C. 154(b) by 0 days.

(21) Appl. No.: 17/055,775

(22) PCT Filed: May 17, 2019

(86) PCT No.: PCT/US2019/032916
§ 371 (c)(1),
(2) Date: Nov. 16, 2020

(87) PCT Pub. No.: WO2019/222659
PCT Pub. Date: Nov. 21, 2019

(65) Prior Publication Data
US 2021/0205180 A1    Jul. 8, 2021

Related U.S. Application Data

(60) Provisional application No. 62/673,299, filed on May 18, 2018.

(51) Int. Cl.
*A61J 7/04* (2006.01)
*A61J 7/00* (2006.01)
(Continued)

(52) U.S. Cl.
CPC .............. *G16H 20/13* (2018.01); *A61J 7/0084* (2013.01); *A61J 7/0481* (2013.01); *G16H 10/60* (2018.01); *G16H 40/67* (2018.01)

(58) Field of Classification Search
CPC ...... A61J 7/0481; A61J 7/0084; G16H 40/67; G16H 10/60; G16H 20/13; G06K 9/00013
See application file for complete search history.

(56) References Cited

U.S. PATENT DOCUMENTS

| 5,142,484 A * | 8/1992 | Kaufman | ............... G16H 20/13 222/638 |
| 7,978,564 B2 * | 7/2011 | De La Huerga | .. A61M 5/16827 700/242 |

(Continued)

OTHER PUBLICATIONS

Benchoff. Hackaday Prize Semifinalist: Smart Medication Dispenser. Sep. 8, 2015. Retrieved Mar. 6, 2023 at https://hackaday.com/2015/09/08/hackaday-prize-semifinalist-smart-medication-dispenser/.

(Continued)

*Primary Examiner* — Michael Collins
(74) *Attorney, Agent, or Firm* — WILSON SONSINI GOODRICH & ROSATI

(57) ABSTRACT

Disclosed herein are patient-side medical devices comprising a plurality of drawers adapted to receive or dispense a medication, at least one visual display, and at least one biometric sensor for acquiring biometric data of a subject. Further the patient-side medical device can comprise a processor configured to change, based at least in part on a measurement: a medication dispensing schedule: a medication: or a dosage of a medication. In some embodiments, a biometric sensor can be a fingerprint reader, a retinal scanner, or facial recognition reader. In some embodiments, a biometric sensor can be a fingerprint reader.

41 Claims, 18 Drawing Sheets

(51) Int. Cl.
    *G16H 20/13*    (2018.01)
    *G16H 10/60*    (2018.01)
    *G16H 40/67*    (2018.01)

(56) References Cited

U.S. PATENT DOCUMENTS

| | | | | |
|---|---|---|---|---|
| 8,068,934 B2 * | 11/2011 | Saltsov | A61J 7/0481 | 221/121 |
| 8,648,891 B2 * | 2/2014 | Terrill | B41J 29/13 | 347/222 |
| 8,874,260 B2 * | 10/2014 | Saltsov | A61J 7/0076 | 700/240 |
| 9,475,633 B2 * | 10/2016 | Hoover | A61J 7/0418 | |
| 9,524,377 B2 * | 12/2016 | Saltsov | A61J 7/0076 | |
| 10,360,751 B2 * | 7/2019 | Berg | G16H 70/20 | |
| 10,453,572 B1 * | 10/2019 | Brooks | G16H 40/40 | |
| 11,410,764 B1 * | 8/2022 | Rosomoff | A61J 7/0481 | |
| 2003/0120384 A1 * | 6/2003 | Haitin | A61G 12/001 | 700/242 |
| 2004/0186357 A1 * | 9/2004 | Soderberg | G16H 30/20 | 600/300 |
| 2005/0288571 A1 * | 12/2005 | Perkins | A61B 5/742 | 600/407 |
| 2010/0030374 A1 * | 2/2010 | Saltsov | A61J 7/0481 | 700/231 |
| 2010/0228566 A1 * | 9/2010 | Taylor | G16H 20/13 | 700/235 |
| 2012/0101630 A1 * | 4/2012 | Daya | G16H 50/20 | 700/231 |
| 2012/0259456 A1 * | 10/2012 | Saltsov | G16H 20/13 | 700/236 |
| 2012/0316405 A1 * | 12/2012 | Taylor | G16H 20/13 | 600/300 |
| 2013/0088328 A1 | 4/2013 | DiMartino et al. | | |
| 2014/0025199 A1 * | 1/2014 | Berg | G07F 17/0092 | 700/232 |
| 2014/0278508 A1 * | 9/2014 | Akdogan | H04N 7/188 | 705/2 |
| 2015/0105903 A1 * | 4/2015 | Denny | G16H 40/67 | 715/740 |
| 2016/0089303 A1 * | 3/2016 | Latorraca | A61J 7/0084 | 312/333 |
| 2017/0076060 A1 | 3/2017 | Pilkington et al. | | |
| 2018/0008498 A1 * | 1/2018 | Sciacchitano | B62B 5/0096 | |
| 2019/0343415 A1 * | 11/2019 | Saha | A61B 5/7282 | |
| 2020/0335192 A1 * | 10/2020 | Tupler | A61J 7/0454 | |
| 2020/0410433 A1 * | 12/2020 | Rahilly | G06Q 50/08 | |

OTHER PUBLICATIONS

PCT/US2019/032916 International Preliminary Report on Patentability dated Dec. 3, 2020.
PCT/US2019/032916 International Search Report and Written Opinion dated Jul. 24, 2019.

* cited by examiner

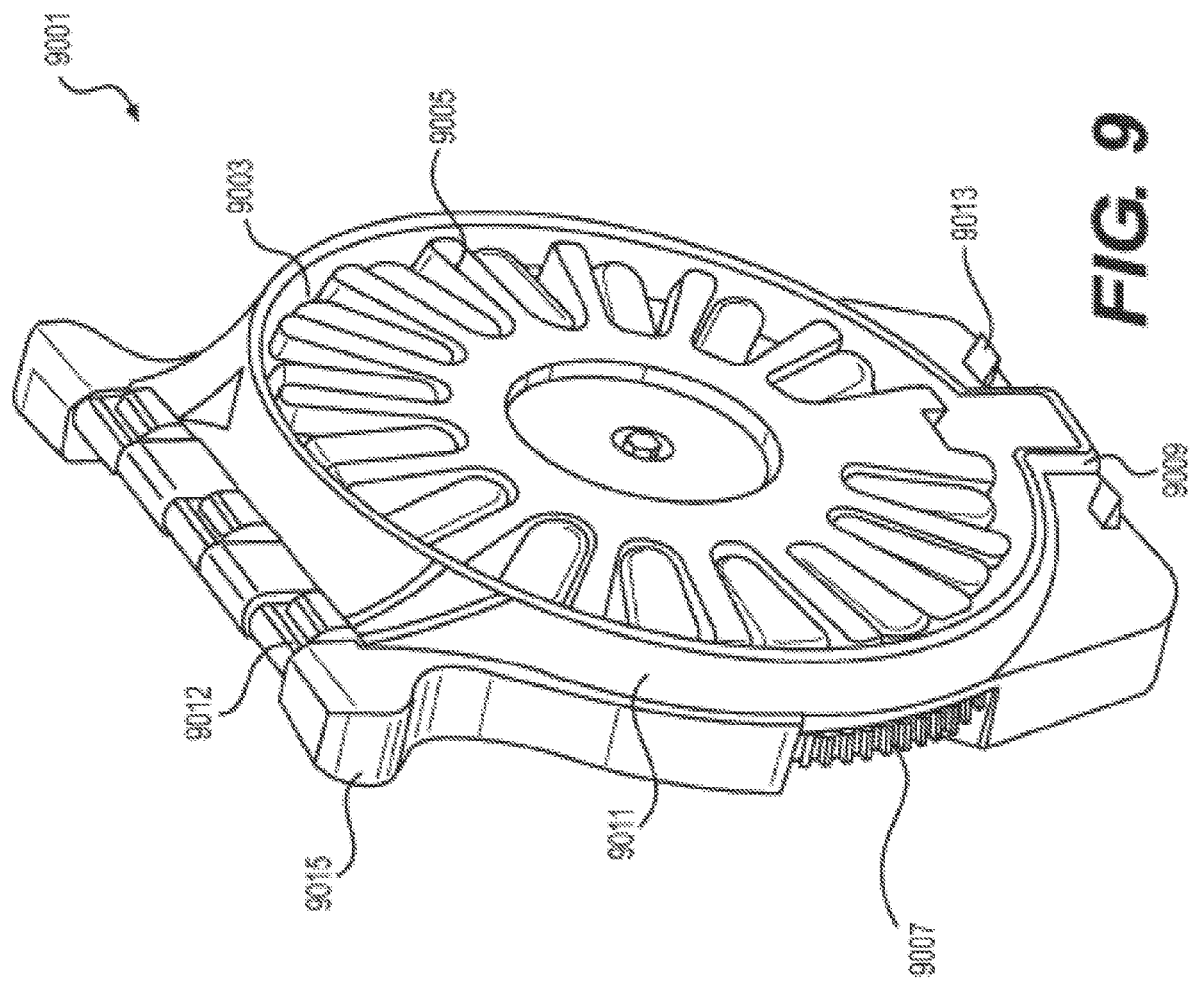

SYSTEM AND DEVICE FOR REMOTE MONITORING

CROSS-REFERENCES TO RELATED APPLICATIONS

This application claims the benefit of U.S. Provisional Application No. 62/673,299 filed on May 18, 2018, the contents of which are incorporated herein by reference in their entirety.

BACKGROUND

Medication treatment regimens can become increasingly complex and difficult for a patient to follow, let alone for a medical professional to reliably monitor a patient's health status and compliance with the treatment regimen. Timely assessment of patient's health status depends on both real-time (or near real-time) measurement of the patient's vital signs, and timely review of the measurements by one or more medical professionals.

SUMMARY

Provided herein are systems, methods and devices for prescribing medications. Provided herein are systems, methods and devices for reliably monitoring subjects. Disclosed herein are patient-side medical devices. In some embodiments, a patient-side medical device can comprises a plurality of drawers adapted to receive or dispense a medication. In some embodiments, a patient-side medical device can comprises at least one visual display. In some embodiments, a patient-side medical device can comprise at least one biometric sensor for acquiring biometric data of a subject. A patient-side medical device can comprise a processor configured to change, based at least in part on a measurement: a medication dispensing schedule; a medication; or a dosage of a medication. In some embodiments, a biometric sensor can be a fingerprint reader, a retinal scanner, or facial recognition reader. In some embodiments, a biometric sensor can be a fingerprint reader. In some embodiments, a biometric data can be acquired prior to dispensing a medication to a subject. In some embodiments, a biometric data can be acquired prior to administering a medication to a subject. In some embodiments, a biometric data can be acquired prior to dispensing a medication to a subject and after administering the medication to the subject. In some cases, a biometric data disclosed herein authenticates a subject. In some embodiments, a visual display disclosed herein can comprise an animated icon indicating authentication of a subject. In some cases, a patient-side medical device disclosed herein may not dispense a medication to a subject prior to authenticating the subject. The patient-side medical device can be in communication with a peripheral device. The communication can be wireless. In some embodiments, a peripheral device can comprise a global positioning system (GPS), blood pressure monitor, a blood glucose monitor, a CPAP machine, an electrocardiogram device, a spirometer, pulse oximeter, digital scale, or a thermometer. The measurement disclosed herein can be generated by the peripheral device. In some embodiments, a measurement can be a blood pressure measurement of the subject. In some embodiments, a measurement can be a blood glucose level of a subject. In some embodiments, measurement can be a blood oxygen level of a subject. In some embodiments, a measurement can be a blood glucose level of a subject. In some embodiments, a measurement can be a sinus rhythm of a subject. In some embodiments, sinus rhythm can be a normal sinus rhythm, sinus tachycardia, sinus bradycardia, atrial fibrillation, atrial flutter, ventricular tachycardia, or a ventricular fibrillation. In some embodiments, a measurement can be stored on a patient-side medical device. In other embodiments, a measurement disclosed herein can be transmitted to a database or server. In some embodiments, a database or server can be a cloud based database or server. A measurement disclosed herein can be compared to a reference. In some embodiments, a measurement can be automatically compared to a reference by a computer. In some embodiments, a measurement disclosed herein can be compared to a reference by a medical professional. In some embodiments, a reference can be a range. In some embodiments, a measurement can be within a range. In some embodiments, a measurement can be outside a range. In some embodiments, a change disclosed herein can comprise an adjustment of a medication dispensing schedule. In some embodiments, a change disclosed herein can comprise an adjustment of a medication. In some embodiments, a change disclosed herein can comprise an adjustment of a dosage of a medication. In some embodiments, a patient-side medical device can be configured to be stored in a transportation system. The transportation system can be a plane. In some embodiments, a transportation system can be a terrestrial vehicle. In some embodiments, a patient-side medical device can be in communication with a medical profession. In some embodiments, a medical profession disclosed herein can be remote from a patient-side medical device. In some embodiments, a patient-side medical device can be portable. The drawers can contain at least 70 individually distinct medications. In some embodiments, drawers can contain at least 200 individually distinct medications.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 9 shows a medication dispenser cartridge according to an embodiment of the present approach;

DETAILED DESCRIPTION

Figure 1:
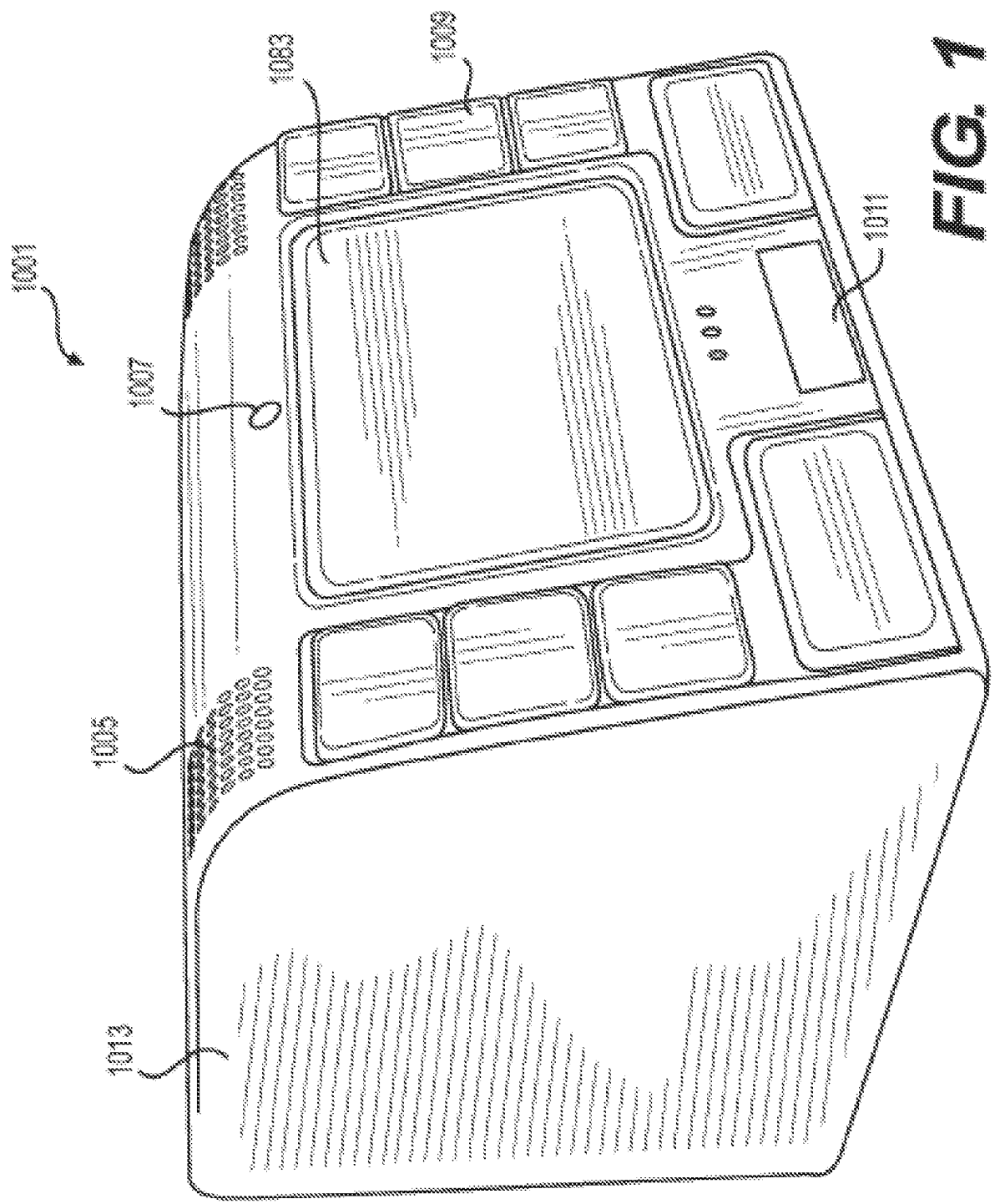
FIG. 1 is an exemplar embodiment of a patient-side device.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The following description sets forth exemplary embodiments of the present approach. The description is not to be taken in a limiting sense, and is made merely for the purpose of illustrating the general principles of the present approach.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. The term "patient-side device," "patient-side health management device," "remote monitoring device," and "pill dispensing patient-side device" may be used interchangeably.

The term "cloud" as used herein can refer to cloud computing. Cloud computing can be an Internet-based computing that can provide shared processing resources and data to computers and other devices on demand. In some cases, cloud computing can entail a sharing of resources (e.g. data) over a network.

The term "Bluetooth" as used herein can refer to a global wireless communication standard that connects devices together over a certain distance. A Bluetooth device can use radio waves instead of wires or cables to connect to another device. In some cases, a device can contain a tiny computer chip with a Bluetooth radio and software that can allow it to connect. In some instances, two Bluetooth devices can be paired in order to communicate. Communication between Bluetooth devices can occur over short-range, ad hoc networks known as piconets. A piconet can be a network of devices connected using Bluetooth technology. In some instances, the network can range from two to eight connected devices or more. When a network is established, one device can take the role of the master while other devices can act as slaves. Piconets can be established dynamically and automatically as Bluetooth devices enter and leave radio proximity. In some embodiments, a Bluetooth core specification can be a Bluetooth basic rate/enhanced data rate (BR/EDR) core specification. In some embodiments, a Bluetooth core specification can be a Bluetooth core specification with low energy functionality. In some embodiments, a Bluetooth core specification can be a Bluetooth Smart core specification.

Remote Monitoring Devices

It should be apparent from the following discussion and drawings that embodiments of the present approach provide more than a pill dispenser. The present approach may provide a multi-purpose health care hub with not only a pill dispensing and verification mechanism, but also an audio-video interface that can support remote, real-time interaction between a patient and a medical professional. Embodiments may also provide data-gathering peripheral devices that can be used to collect vital sign data and other medically relevant data for use by medical professionals who not only can use the embodiments to verify delivery of medications, but also can remotely assess the health of a patient, and based on their assessments of the collected data, take immediate action, which can include making changes to medication dispensing orders, and transmit those orders to the dispensing controller within the patient-side device.

The present approach may relate to health management devices and systems that solve a growing problem in the medical field relating to the delivery of medications and monitoring patient compliance with medication treatment regimens. One of the biggest problems encountered after surgery, for example, may be discovering and achieving an ideal dosage and delivery schedule of necessary medications. Today, problems resulting from improper medication dosage often cannot be recognized or resolved until a patient returns to the hospital. By that time, the patient may already be exhibiting severe symptoms relating to, among other things, failure to comply with a medication treatment regimen.

Embodiments of the present approach may address such problems by, for example, (1) providing a medication delivery system that delivers medications to patients in a controlled and verified fashion; (2) allowing real-time interaction between medical health professionals and patients; (3) generating real-time physiological measurements relating to a patient's health and well-being; and (4) enabling real-time assessment and revision to medication dosage regimes, which can then be made immediately available to the patient. Some embodiments may also provide simultaneous recording of patient vital signs, and permit medical professionals to conduct real-time, interactive assessments of patients on an as-needed basis.

Embodiments of the present approach may comprise a remote monitoring device with one or more of the following elements: (1) an automated pill dispenser with various security and verification features; (2) a hub for collecting patient vital signs, among other measurements, and relaying data to medical professionals; (3) audio and video observation and/or recording of medication delivery to a patient; (4) recording all medication delivery and vital sign data; (5) automated reporting of collected data to medical professionals via supervisory embodiments; (6) analysis of collected data, on a patient-by-patient basis, as well as on a mass population basis; and (7) real-time, interactive, audio and video interaction between a patient, medical health professionals, and other caregivers and/or guardians. The remote monitoring device may be a patient-side health management device.

Although "pill" is used herein, it may be understood that the medication may be formulated as any form, for example, but not limited to, a capsule, tablet, juice, powder, suspension, emulsifier, granules, troch, pill, suspension, spirit, or syrup. The patient may be the user of the patient-side health management device. The user of the patient-side health management device may be any living beings, for example, amphibians, reptiles, birds, mammals, fishes, insects, spiders, crabs, snails, or plants. The user of the patient-side health management device may be the patient that needs medical care, medical professionals, the relatives of the patient that needs medical care, or anyone who uses the patient-side health management device.

The patient-side health management device may deliver information of the medication through text, image, voice, or video. The patient-side health management device may deliver the information of the medication through video while the patient-side health management device is on. The information of the medication may be an amount, quantity, mass, weight, and/or volume of the medication inside the device. The information may be facts about the medication. The facts about the medication may be the name of the medication, the function of the medication, the remaining dose of the medication, the time for a scheduled dose, side effects and other information related to the patient or the medication, scientific background of the medication, additional symptoms triggered by the medication, warnings of recent deaths, latest research on the medication or relevant conditions, and any updates about the medication.

The patient-side health management device may be used as a food dispensing diet device. If a patient-side health management device is used as a food dispensing diet device, the information delivered may comprise, but not limited to, the user's diet plan, the user's food intake per day based on the diet plan, the user's water intake, the nutrition information of the user's food intake, the price of the user's food intake, and the recipe of making the user's food. The patient-side health management device may be used for a smoke cessation program. If the patient-side health management device is used for a smoke cessation program, the information delivered may comprise facts of prescription drugs, relevant insurance programs, nicotine over-the-counter products, quit lines, on-line resources, relevant education programs, hospitals, and support groups.

The patient-side health management device may be used as a medical marijuana dispensing device. A verification area may be integrated with the patient-side health management device to ensure dispensing medical marijuana to the right patient. The verification area can facilitate visual identification of medical marijuana to dispense, such as, for instance, automated identification or separate confirmation by a medical professional. The verification area may include a camera with an automated visual object recognition module for the medical marijuana that can be identified by appearance. The verification area may also include sensors to identify the medical marijuana if it cannot be easily identified by appearance. The verification area may also provide a verification process conducted by medical professional or other individuals prior to delivery to the patient. The medical professionals may use the video camera to verify the medical marijuana is delivered to the patient. The verification area may comprise a scanner or input means to identify the patient. The scanner or input means may be used to ensure it is the right person to receive the medical marijuana. The scanner or input means may be a reader. The reader may be, but not limited to, a facial recognition reader, a voice recognition reader, or a biometric reader. The biometric reader may be a fingerprint reader.

The patient-side health management device may comprise a plurality of extra storage components. The extra storage components may be used to store non-medical items. The non-medical items may be a gun, a safe, cash, jewelries, check, credit cards, documents, keys, and social security cards. The extra storage components may be operatively coupled with the verification area. The verification area may comprise a scanner or input means to identify the user. The scanner or input means may be used to ensure it is the right person to take out the non-medical items. The scanner or input means may be a reader. The reader may be, but not limited to, a facial recognition reader, a voice recognition reader, or a biometric reader. The biometric reader may be a fingerprint reader.

The patient-side health management device may collect data related to patient's vital signs. The patient-side health management device may provide alerts to the patient if the patient's vital signs are outside a range specified by a medical professional. The medical professionals may be doctors, physicians, and nurses. The vital signs may be measurements of the patient's basic body functions. The vital signs may include body temperature, pulse rate, respiration rate, blood pressure or any measurements described herein.

The range of the body temperature specified by a medical professional may be from about 96 degrees Fahrenheit to about 103 degrees Fahrenheit. In some cases from 96 degrees Fahrenheit to 99 degrees Fahrenheit, 97.2 degrees Fahrenheit to 99 degrees Fahrenheit, 97.4 degrees Fahrenheit to 99 degrees Fahrenheit, 97.6 degrees Fahrenheit to 99 degrees Fahrenheit, 97.8 degrees Fahrenheit to 99 degrees Fahrenheit, 97.8 degrees Fahrenheit to 99.2 degrees Fahrenheit, 97.8 degrees Fahrenheit to 99.4 degrees Fahrenheit, 97.8 degrees Fahrenheit to 99.6 degrees Fahrenheit, 97.8 degrees Fahrenheit to 99.8 degrees Fahrenheit, 97.8 degrees Fahrenheit to 100 degrees Fahrenheit, 97.8 degrees Fahrenheit to 100.2 degrees Fahrenheit, 97.8 degrees Fahrenheit to 100.4 degrees Fahrenheit, 98 degrees Fahrenheit to 99 degrees Fahrenheit, 100 degrees Fahrenheit to 101 degrees Fahrenheit, or 101 degrees Fahrenheit to 102.5 degrees Fahrenheit.

The range of the pulse rate specified by a medical professional may be from about 50 to about 160 beats per minutes. In some example, 60 to 100 beats per minute, 40 to 100 beats per minute, 45 to 100 beats per minute, 50 to 100 beats per minute, 55 to 100 beats per minute, 65 to 100 beats per minute, 65 to 110 beats per minute, 65 to 120 beats per minute, 40 to 70 beats per minute, 40 to 80 beats per minute, 40 to 90 beats per minute, 50 to 70 beats per minute, 50 to 80 beats per minute, 50 to 90 beats per minute, 60 to 70 beats per minute, 60 to 80 beats per minute, 60 to 90 beats per minute, 55 to 60 beats per minute, 55 to 65 beats per minute, 55 to 70 beats per minute, 50 to 75 beats per minute, 55 to 85 beats per minute, 50 to 90 beats per minute, or 55 to 95 beats per minute.

The range of the respiration rate specified by a medical professional may be from about 6 to about 50 breaths per minute. For example, 12 to 16 breaths per minute, 12 to 17 breaths per minute, 12 to 18 breaths per minute, 12 to 19 breaths per minute, 12 to 20 breaths per minute, 13 to 15 breaths per minute, 13 to 16 breaths per minute, 13 to 17 breaths per minute, 13 to 18 breaths per minute, 13 to 19 breaths per minute, 13 to 20 breaths per minute, 14 to 16 breaths per minute, 14 to 17 breaths per minute, 14 to 18 breaths per minute, 14 to 19 breaths per minute, 14 to 20 breaths per minute, 15 to 16 breaths per minute, 15 to 17 breaths per minute, 15 to 18 breaths per minute, 15 to 19 breaths per minute, or 15 to 20 breaths per minute, The range of the blood pressure specified by a medical professional may be systolic of less than 120 and diastolic of less than 80, systolic of less than 119 and diastolic of less than 79, systolic of less than 118 and diastolic of less than 78, systolic of less than 117 and diastolic of less than 77, systolic of less than 116 and diastolic of less than 76, systolic of less than 115 and diastolic of less than 75, systolic of less than 114 and diastolic of less than 74, systolic of less than 113 and diastolic of less than 73, systolic of less than 112 and diastolic of less than 72, systolic of less than 111 and diastolic of less than 71, systolic of less than 110 and diastolic of less than 70, systolic of less than 109 and diastolic of less than 69, systolic of less than 108 and diastolic of less than 68, systolic of less than 120 and diastolic of less than 75, systolic of less than 120 and diastolic of less than 70, or systolic of less than 110 and diastolic of less than 80. In some cases, a blood pressure can be less than about 120 systolic mmHg and less than about 80 diastolic mm Hg. In some cases, a blood pressure can be greater than about 120 systolic mmHg and greater than about 80 diastolic mm Hg.

The medical professional may adjust and/or customize vital sign ranges. The adjustment may be made based on the patient's physical conditions, medical histories, occupations, ages, sexes, races, nationalities, or feedback/reports or recommendations from the patient-side health management device etc. The patient's physical conditions may include the patient vital signs. The medical professionals may obtain any information from the patient remotely. The medical professionals may obtain any information from the patient without patient visiting the medical professionals' working places. The working places may be, but not limited to, the hospitals, clinics, and offices. The patient's physical conditions may be monitored through the patient-side health management device or one or more apparatus operatively coupled with the patient-side health management device. The one or more apparatus may be sensors or medical instruments.

Medical professionals may change a medication prescription based on the patient's physical conditions, medical histories, occupations, ages, sexes, races, nationalities, etc. The medical professionals may change the medication prescription based on the patient's physical conditions measured by the patient-side device. The medical professionals may change a medication script on the patient-side device. In order to do so, the medical professionals may connect the medical professional-side device with the patient-side device. Based on patient's information (e.g. vital signs) provided through the patient-side device, the medical professionals may change the dosing of a given medication to the patient on the patient-side health management device.

Materials of Use

The patient-side device may be made with biologically acceptable materials suitable for medical applications. For example, the materials of the patient-side device may be cellophane, vinyl, acetate, polyethylene acrylic, butyl rubber, ethylene-vinyl acetate, natural rubber, a nitrile, silicone rubber, a styrene block copolymer, a vinyl ether, or a tackifier. The patient-side device may be fabricated with materials such antimicrobial and/or antiseptic materials, including, but not limited to: sodium bicarbonate; hydrogen peroxide; benzalkonium chloride; chlorhexidine; hexachlorophene; iodine compounds; beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anticancer drugs; anti-malarial drugs; anti-tuberculosis drugs; anti-leprotic drugs; anti-protozoal drugs and combinations thereof.

One or more components of the patient-side device may be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof, stainless steel alloys, commercially pure titanium, titanium alloys, silver alloys, copper alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The patient-side device may include an automated pill dispenser that dispenses one or more pills (e.g., medications in tablet, capsule, caplet, or other forms as are known in the art) from a bank of pill reservoirs. The bank of pill reservoirs may be contained within a locked or closed portion or housing of the patient-side device, thereby reducing the likelihood of tampering with and theft of medications. Each pill reservoir in the patient-side device can be configured to receive a single pill cartridge containing a predetermined number of pills. Pills can be different sizes, shapes, and configurations.

Pill Dispensing Feature

The bank of pill reservoirs in a patient-side device can be configured with reservoirs of different sizes (e.g., small, medium, large), to accommodate various sizes and kinds of pill cartridges and pills. The pill reservoir may be formed having any shape, design, depth, and/or size. Examples of possible shapes or designs include but are not limited to: mathematical shapes, two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, miscellaneous surfaces, riemann surfaces, box-drawing characters, cuisenaire rods, geometric shapes, shapes with metaphorical names, symbols, unicode geometric shapes, shapes based on math symbols characters from any language history music art science religion, or any other form.

Some embodiments may have a plurality of the same pill reservoirs, and thus may be configured for use with a plurality of pill cartridges of the same shape and size. Other embodiments may have a variety of pill reservoirs, and thus may be used with various combinations of pill cartridges. The pill reservoirs may be arranged in a variety of patterns and/or configurations, including a rectangular matrix or array, a circular "carousel" array, as well as other configurations, as should be appreciated by those skilled in the art.

For example, some embodiments may feature a rectangular array of pill reservoirs, such that each column of reservoirs may be configured to hold a particular size and/or type of pill (or pill cartridge). As one example, two columns may be configured to hold small pills or a first type of cartridge, two columns may be configured to hold medium pills or a second type of cartridge, and one column may be configured to hold large pills or a third type of cartridge. Some reservoirs can be configured to hold a plurality pills that are prescribed for simultaneous (or nearly simultaneous) administration. Other reservoirs can be configured to hold supplemental pills that can be prescribed on an as-needed basis, such as, for example, when a patient's vital signs or other measurements indicate the need for a supplemental medication.

Pill cartridges can include an identifier, such as a barcode, QR code, or other symbol, to indicate the contents of the cartridge. The barcode may be a UPC barcode, EAN barcode, Code 39 barcode, Code 128 barcode, ITF barcode, CodaBar barcode, GS1 DataBar barcode, MSI Plessey barcode, QR barcode, Datamatrix code, PDF417 code, and Aztec barcodes. Embodiments of the patient-side device can include a sensor, such as a barcode reader, that scans the identifier on a pill cartridge when the cartridge may be inserted into a corresponding reservoir, or during operation. The barcode may define elements such as the version, format, position, alignment, and timing of the barcode to enable reading and decoding of the barcode. The remainder of the barcode can encode various types of information in any type of suitable format, such as binary or alphanumeric information.

The identifier can correspond to a serial number, description, or other code or information that identifies the cartridge, its source, its contents, the prescribing doctor, the filling pharmacy, and the like. The identifier can also include information describing or referencing other information (such as in a database) describing the type of pills contained in the cartridge (e.g., tablet, capsule, caplet), the size of pills contained in the cartridge, the number of pills contained in the cartridge, the date of manufacture of the pills, the medication contained in the pills, the dosage and/or regimen for each pill, and other information about the pills, including recommended storage temperature, recommended storage duration, and recommended destroy and/or replace date. The identifier can also include the name of the patient(s) intended to receive the pills contained in the cartridge, as well as instructions relating to operation of the patient-side device, information to display to the patient, and information to make available to a medical professional, as examples. If the identifier is a QR code, the QR codes can be optically captured and read by a QR code reader. The QR code can have various symbol sizes as long as the QR code can be scanned from a reasonable distance by an imaging device. The QR code can be of any image file format (e.g. EPS or SVG vector graphs, PNG, TIF, GIF, or JPEG raster graphics format). The QR code can be based on any of a number of standards.

Some embodiments of the patient-side device can be configured to receive and dispense pill cartridges for one patient, whereas other embodiments may be configured for use with a plurality of patients. For example, the patient-side device may include a scanner or input means to identify the patient and determine the pill(s) to dispense for that patient. The scanner or input means may be used to ensure it is the right person to use the patient-side device. The scanner or input means may be a reader. The reader may be, but not limited to, a facial recognition reader, a voice recognition reader, or a biometric reader. The biometric reader may be a fingerprint reader.

In other embodiments, a unique patient identifier can be based on biometric data of the patient. In one such example case, biometric capability (e.g., facial and/or voice recognition, retina scan, blood type monitor, finger print scan can be used to identify specific subject. In some embodiments, such identification can be necessary for a subject to access and use a device/software disclosed herein.

Pill cartridges may be sealed to ensure product freshness, integrity, and security, as well as to control environmental factors (e.g., humidity, temperature). The seal may be broken upon insertion of the cartridge into a pill reservoir, for example, or upon closure of a lid covering the pill reservoir, as another example. The lid may be locked in a number of manners, as should be apparent to those of skill in the art. Pills can be dispensed from a set of given pill cartridges and/or pill reservoirs according to a schedule or regimen set for a patient, which may be sent to the patient-side device electronically, set forth in one or more identifiers on a cartridge or plurality of cartridges, or otherwise made available to the patient-side device.

Each reservoir may be temperature controlled. The temperature may be increased or decreased according to the ambient temperature as well as the ideal prescribed temperature of the pills in a cartridge residing in the reservoir. Reservoirs may therefore be configured to include one or more of a temperature sensor, a humidity sensor, and individualized temperature control mechanisms as are known in the art. The entire pill reservoir may also be configured with a single temperature control mechanism to control the temperature of all pill reservoirs in the health management device.

Medication can be dispensed using a variety of dispensing technologies, including, for example, a vertical rotating wheel mechanism in a cartridge, in which each pill may be funneled by gravity from a slot in the rotating wheel to a chute beneath the cartridge. Some embodiments may also use a vibrating mechanism to ensure the medication is dispensed. Once a pill has exited the cartridge chute and dropped into a landing area, some embodiments may include a further processing stage for, as an example, pill verification, prior to allowing the pill to travel to a dispensing area. A rotating wheel mechanism can be installed in a pill reservoir for some embodiments, and may be integrated into a pill cartridge in some embodiments.

Embodiments of the invention can include a set of sensors that track the loading of pill cartridges (or collection of pills) into a pill reservoir, and track the dispensing operation of each pill. Sensors can track a pill as it leaves a pill cartridge, as it moves through a dispensing mechanism, and as it travels to a verification area and/or dispensing area.

Embodiments of the patient-side device may include additional features to ensure movement of pills as desired. For example, the movement of pills from a reservoir or cartridge, through a dispensing mechanism (such as the rotating wheel described above), and into a verification area or dispensing, area, can be assisted by small puffs of air, such as compressed air, blown into the movement channels to encourage the desired movement. If an embodiment fails to deliver a pill for whatever reason (e.g., a pill gets jammed, a pill gets crushed, a communications network fails, or some other failure), or a data gathering device fails to provide valid data, some embodiments may be configured to alert a medical professional or other third party to contact the patient and inquire about the failure. In some embodiments, the patient-side device may issue a request for maintenance or servicing to determine and repair the problem. In some embodiments, the patient-side device may issue a request for a medical professional to be dispatched to the location within a certain amount of time.

Remote Monitoring Systems

Embodiments may take the form of a system in which one or more pill dispensing patient-side devices as described herein may be interconnected to one or more medical professional-side devices. The patient-side device may also be interconnected to other devices, for instance, enterprise devices. The connection may be in the form of a network supported by the Internet or other distributed network, such as in individual patient homes in communication with a data center, central network, or other professional device. Other embodiments may be implemented in the form of devices connected wirelessly or by wire in a local area network, such as a hospital or other medical treatment facility. Regardless of the implementation, the patient-side devices may communicate with one or more medical professional devices by exchanging data. For example, the patient-side devices may transmit data relating to the patient's pill dispensing history, vital sign measurements, and the like, and the medical professional devices may transmit data relating to modifications in a patient's treatment regimen and the like. In some embodiments, the patient-side and medical professional-side devices may support audio and/or video data exchange, such that medical professionals may engage in live communications with the user (e.g., patient, caretaker, etc.). The live communications may be conducted through multiple platforms. The multiple platforms may comprise, but not limited to, a website, email, text message, Facebook Messenger, Twilio SMS, Skype, Slack, WeChat, Telegram, Viber, Line, Microsoft Team, Cisco Spark, and Amazon Chime.

The pill dispensing patient-side device may be used to collect data from patient side. The collected data may comprise, but not limited to, the patient's medical history, the name of the patient, the birthday of the patient, the nationality of the patient, the residency of the patient, the family doctor of the patient, the phone number of the patient, the email address of the patient, the medication taken by the patient, and the side effect of some medications taken by the patient. The data may also comprise the patient's age, height, weight, BMI, blood pressure, resting pulse, medical history, mental health status, sex, race, ethnicity, diet, or other risk factors such as smoking, drug or alcohol abuse, or potential drug incompatibilities. The data may be used by medical professionals, insurance companies, food distributors, restaurants, or any individual or enterprise that may make usage of the data.

The data may be stored in a database. A database can be stored in computer readable format. A computer processor may be configured to access the data stored in the computer readable memory. A computer system may be used to analyze the data to obtain a result. The result may be stored remotely or internally on storage medium, and communicated to personnel such as medication professionals. The result may be, but not limited to, the patient's further medication intake, the patient's meal plans, the patient's exercise schedule, the patient's annual health check schedule, and/or the patient's health goals. The computer system may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples or wireless communication components can include a Wi-Fi receiver, a component for accessing a mobile data standard such as a 3G or 4G LTE data signal, or a Bluetooth receiver.

All these data in the storage medium may be collected and archived to build a data warehouse. The data warehouse may be used by medical professionals to analyze the prescribed medications and remotely monitor both the patient's compliance with the medication regimen, and the patient's reactions to the medications. The data warehouse may be used to analyze the effects of the medication and provide insight information for further scientific research. The data warehouse may also be used to analyze patient's behavior relevant to taking the medication and provide marketing information to pharmaceutical companies, drug stores, hospitals, and any other enterprises. The data warehouse may be integrated with clinical trial platforms. The patient may participate in one or more clinical trials. The warehouse may allow recognition or identification of new medications or compounds for treating certain kinds of diseases. The warehouse may be mined using Artificial Intelligence tools for stratification.

The computer system may be configured to communicate with an external database. The external database may be, but not limited to, Adverse Drug Effects Database, AHFS Supplemental File, Allergen Picklist File, Average WAC Pricing File, Brand Probability File, Canadian Drug File v2, Comprehensive Price History, Controlled Substances File, Drug Allergy Cross-Reference File, Drug Application File, Drug Dosing & Administration Database, Drug Image Database v2.0/Drug Imprint Database v2.0, Drug Inactive Date File, Drug Indications Database, Drug Lab Conflict Database, Drug Therapy Monitoring System (DTMS) v2.2/DTMS Consumer Monographs, Duplicate Therapy Database, Federal Government Pricing File, Healthcare Common Procedure Coding System Codes (HCPCS) Database, ICD-10 Mapping Files, Immunization Cross-Reference File, Integrated A to Z Drug Facts Module, Integrated Patient Education, Master Parameters Database, Medi-Span Electronic Drug File (MED-File) v2, Medicaid Rebate File, Medicare Plans File, Medical Condition Picklist File, Medical Conditions Master Database, Medication Order Management Database (MOMD), Parameters to Monitor Database, Patient Safety Programs File, Payment Allowance Limit-Part B (PAL-B) v2.0, Precautions Database, RxNorm Cross-Reference File, Standard Drug Identifiers Database, Substitution Groups File, Supplemental Names File, Uniform System of Classification Cross-Reference File, or Warning Label Database.

The computer system can transmit data to a database or server. A database or server can be a cloud server. The computer system can transmit data wirelessly via a Wi-Fi, or Bluetooth connection. The computer system may comprise centralized data processing. The centralized data processing may be cloud-based, internet-based, locally accessible network (LAN)-based, or a dedicated reading center using pre-existent or new platforms. The computer system may comprise one or more software. The software can rely on structured computation, for example providing registration, segmentation and other functions, with the centrally-processed output made ready for downstream analysis. The software may rely on unstructured computation, artificial intelligence or deep learning. The software may rely on unstructured computation, such that data could be iteratively.

The pill dispensing patient-side device may be integrated with an electronic device. The integration may be to promote or ensure compliance. The electronic device may be a portable electronic device. The electronic device may be mobile phones, PCs, tablets, printers, consumer electronics, and appliances. The electronic devices may be wearable devices, including but not limited to, Fitbit, Apple watch, Samsung health, Misfit, Xiaomi Mi band, and Microsoft band. The pill dispensing patient-side device may monitor patient health status and compliance with medication treatment schedules or other regiments. The patient health status may be monitored through one or more sensors of the patient-side device or operatively coupled with the patient-side device. The one or more sensors may include, but not limited to, acoustic sensors, sound sensors, vibration sensors, chemical sensors, electric current sensors, magnetic sensors, radio sensors, moisture sensors, humidity sensors, flow sensors, radiation sensors, imaging sensors, light sensors, optical sensors, pressure sensors, density sensors, thermal sensors, heat sensors, temperature sensors, proximity sensors, GPS, or any sensor described herein. The patient health status may be monitored through the patient-side device or one or more medical instruments operatively coupled with the patient-side device. The one or more medical instruments may include, but not limited to, stethoscope, suction device, thermometer, tongue depressor, transfusion kit, tuning fork, ventilator, watch, stopwatch, weighing scale, crocodile forceps, bedpan, cannula, cardioverter, defibrillator, catheter, dialyzer, electrocardiograph machine, enema equipment, endoscope, gas cylinder, gauze sponge, hypodermic needle, syringe, infection control equipment, an oximeter or oximeters that monitors oxygen levels of the user, instrument sterilizer, kidney dish, measuring tape, medical halogen penlight, nasogastric tube, nebulizer, ophthalmoscope, otoscope, oxygen mask and tubes, pipette, dropper, proctoscope, reflex hammer, or sphygmomanometer.

The devices disclosed herein can be associated with via wires or wirelessly with any one oft a blood pressure monitor, a blood glucose monitor, a CPAP machine, an electrocardiogram device, a battery, or a battery charger. In some embodiments, the device can include an infrared (IR) transmitter and receiver, a radio-frequency identification (RFID) reader, and/or Bluetooth hardware and software components.

The patient health status may include, but not limited to, the vital signs of the patient, the body temperature of the patient, the eyesight of the patient, the blood pressure of the patient, or the pulse of the patient. The medication treatment schedule may include the number of a given medication that may be taken by the patient per day (week, month, or per hour), the name of the medication that the patient may be taken, and the time when the medication may be taken by the patient during a day. The medication may be an over-the-counter medicine, prescribed medicine, vitamin, mineral supplement, or dietary supplement. The dietary supplements may contain one or more dietary ingredients, including vitamins, minerals, herbs, amino acids, and other substances. The pill dispensing patient-side device may monitor when the patient takes the dietary supplement or alert a patient to take or a time until a patient should take an over-the-counter medicine, prescribed medicine, vitamin, mineral supplement, or dietary supplement.

Storage and Database

A patient health status and/or compliance with the medication treatment schedule or other data collected by the device described herein may be stored in a database. The database may be a centralized database. The database may be connected with one or more processors. The one or more processors may analyze the data stored in the database through one or more algorithms. The analysis performed by the one or more processors may include, but not limited to, monitoring the patient's compliance with a reference medication treatment schedule, obtaining the patient health status from the database, obtaining a predicted medication treatment schedule of the patient through one or more algorithms, comparing the reference medication treatment schedule with the predicted medication treatment schedule, and updating the new medication treatment schedule based on the comparison. The one or more processors may provide one or more instructions based on the analysis. The one or more instructions may be displayed on a display screen of the patient-side device. The one or more instructions may comprise requesting the patient to take a given medication according to the predicted medication treatment schedule or informing a patient of a change to a treatment schedule or regimen. The one or more instructions may comprise requesting the patient to take a given medication according to the reference medication treatment schedule. The one or more instructions may comprise requesting the patient to provide his/her health status, or to perform an action or a test.

A database described herein may be connected with one or more servers. The database may be connected with one or more medical professional-side devices through the one or more severs. The database may be connected with at least one patient-side device. The connection may be a wired connection or wireless connection. The medical professional-side device may be in communication with the patient-side devices through the connection. The medical professional-side device may obtain data from the database through the connection. The obtained data may be any information stored in the database. The obtained data may be analyzed by the user of the medical professional-side device.

The user of the medical professional-side device may enter one or more instructions on the medical professional device based on an analysis or data received. Data obtained from the patient-side device or professional-side device may be analyzed by one or more algorithms installed on the medical professional-side device. The one or more instructions may be stored in the database. The one or more instructions may be transmitted to the patient-side device through the one or more servers. The one or more instructions may comprise requesting the patient to take a given medication according to the predicted medication treatment schedule. The one or more instructions may comprise requesting the patient to take a given medication according to the reference medication treatment schedule. The one or more instructions may comprise requesting the patient to provide his/her health status, perform a test or perform an action. The medical professional-side device may transmit medication treatment regimens to the plurality of patient-side devices, and receive medication treatment regimen compliance data from the plurality of patient-side devices. The patient-side device may include at least one port for connecting to one or more apparatus operatively coupled with the patient-side device. The one or more apparatus may be sensors or medical instruments. The medical professional-side device may receive measurement data generated from the patient-side device or one or more apparatus operatively coupled with the patient-side device.

A database described herein may be connected with one or more enterprise devices. The enterprise devices may be used by any enterprises or companies, including, but not limited to, insurance companies, pharmaceutical companies, grocery stores, food distributors, and restaurants. The enterprise device may be in communication with the patient-side devices through a connection. The connection may be wired or wireless. The enterprise device may obtain data from the database through the connection. The obtained data may be any information stored in the database. The obtained data may be analyzed by a user of the enterprise device. The user of the enterprise device may enter one or more instructions on the enterprise device based on the analysis. The obtained data may be analyzed by one or more algorithms installed on the enterprise device or on the patient-side device. The one or more instructions may be stored in the database. The one or more instructions may be transmitted to the patient-side device through the one or more servers. The one or more instructions may be providing rewards to patients based on a plurality of criteria. The plurality of criteria may be, for instance, whether the patient follows the medication treatment or regimen, whether the patient exercises according to the exercise schedule, whether the patient chooses healthy foods to eat, a period of cessation from an activity or a period of performing an activity or any type of criteria measuring whether the patient may be healthy or try to be healthy. The rewards may be, but not limited to, a discounted or increase in price or rate of an activity or event or a coupon or other reinforcing/deterring actions, for example a discounted or increased rate for insurance policies, a discounted price for food purchase in grocery stores, or a discounted price for medications sold by pharmaceutical companies.

In other cases, data collected from individuals using or who have used a device described herein or a peripheral device associated herewith can be stored through a variety of different mediums. In some embodiments, an integrated hard drive can be used to store data. In some embodiments, an integrated hard drive can be electronically connected to a patient-side medical device or a medical profession-side device. In some specific embodiments, an integrated hard drive can be a solid state hard drive. In some embodiments, an integrated hard drive can be a SATA hard drive. In some embodiments, a hard drive can be an eSATA hard drive. In some embodiments, an integrated hard drive can be removed from a device described herein.

In some embodiments, an external hard drive can be used to store data. In some embodiments, an external hard drive can be connected to a device described herein. In some embodiments, an external hard drive can be connected using a USB connection. In some embodiments, a USB connection can be a USB 2.0 connection. In some embodiments, a USB connection can be a USB 3.0 connection. In some embodiments, an external hard drive can be a solid state hard drive. In some embodiments, a device described herein can comprise an SD card slot. In some embodiments, data can be stored on an SD card.

In some embodiments, a removable storage medium can be used to store data. In some embodiments, a removable storage medium can be a USB flash drive, e.g., in which a USB flash drive can be electronically connected to a device described herein via a USB port. In some embodiments, a removable storage medium can be a memory stick. In such an embodiment, a memory stick can be electronically connected a device described herein via a memory stick adapter. In some embodiments, a removable storage media can be a compact disk (CD). In some specific embodiments, a CD can be a DVD or Blu-ray disk, e.g., a CD writer can be electronically connected to a device described herein via a USB port.

In some embodiments, data can be stored wirelessly. In some embodiments, data can be stored on a wireless hard drive. In some embodiments, data can be stored on a network-attached storage (NAS). In some embodiments, data can be stored using a cloud-based storage service. In some embodiments, data can be transmitted to one or more servers, databases, storage units including network attached storage units, volumes, or any combination thereof.

Portability

The pill dispensing patient-side device may comprise a travel pack which may be used when the user is traveling. The travel pack may comprise a portable medication holder. The travel pack may be connected to one or more medical professional-side devices or platforms. The connection may be in the form of a network supported by the Internet or other distributed network, such as in individual patient homes in communication with a data center, central network, or other professional device. Other embodiments may be implemented in the form of devices connected wirelessly or by wire in a local area network, such as a hospital or other medical treatment facility. The connection may be through a wireless card. The travel pack may comprise an alert system. The alert system may inform the user when to take the medication.

The patient-side device may be placed in a residence. The residence may be an apartment, condo, townhouse, or single family house. The patient-side device may be operatively coupled with one or more communication devices. The communication devices may be electronic devices. The communication devices may be used for communicating personalized medicine in the residence. The patient-side device may be operatively coupled with one or more delivery devices. The delivery devices may be used for delivering one or more personalized medicine in the residence.

The patient-side device may send signals to a patient who lives in the residence. The signals may be in the form of movement (vibration), visual (flashing of lights of same or different colors) and/or auditory (sounds, increasing or decreasing volume). The forms of the signal may be changed by the patient. The signal may be presented to the patient through a speaker or a display screen. The speaker and/or display may be operatively coupled with an electronic device. The speaker and/or display may be integrated with an electronic device. The electronic device may be a small alert apparatus. The electronic device may be a portable electronic device. The electronic device may be mobile phones, PCs, tablets, printers, consumer electronics, a wearable device or appliances. The electronic devices may be wearable devices, including but not limited to, Fitbit, Apple watch, Samsung health, Misfit, Xiaomi Mi band, and Microsoft band. The signal may be an alert that requests the patient to come to the patient-side device and/or take a given medication according to a selected or predetermined medication treatment schedule or regimen. The signal may be nurse/medical profession alert to tell a patient to come to the device and/or take a given medication. The signal may be switched on and off by a patient. The signal may be triggered by one or more events. The one or more events may include, but not limited to, time for the patient to take medications, time has passed for the patient to take medications, and time for checking the patient's health status, a countdown to perform an action, an alert to perform, continue or stop an action. A patient may choose a subset of the events to trigger the signals.

The patient-side device may not be placed in a residence. If the patient-side device is not placed in a residence, the patient-side device may be placed in a transportation system. A transportation system may be, but not limited to, an aircraft, airplane, automobile, battleship, bus, bullet train, bike, cab, canoe, cargo ship, compact car, truck, elevated railroad, ferry, fishing boat, jet boat, kayak, limo, minibus, minivan, sail boat, school bus, tank, train, van, or yacht. In some cases, the patient-side device can be configured to fit the area in which the device may be used.

The patient-side device may be dimensioned to fit in a rolling cart used in the transportation system. The rolling cart may be food cart used in the transportation system. The rolling cart may be an airplane food cart. The patient-side device may comprise one or more apparatus to check the patient's health status and/or measure the patient's physical conditions (e.g., vital signs). The apparatus may be sensors and or medical instruments. The apparatus may be integrated with the patient-side device. The apparatus may also be portable and operatively coupled with the patient-side device.

The patient-side device may enable the communication between an individual in the transportation system and medical professionals who are not in the transportation system. The individual in the transportation system may be a subject that needs medical care. The individual in the transportation system may be a service provider working for the transportation system. The individual in the transportation system may also be subjects who are in the transportation system but do not need medical care. The communication may be a wireless connection. The wireless connection may include a Wi-Fi receiver, a component for accessing a mobile data standard such as a 3G or 4G LTE data signal, or a Bluetooth receiver. The communication may comprise any information related to the individual in the transportation system. The communication may comprise any information related to the individual's health. The communication may be in the form of text, image, video, voice or a combination thereof. The information may include the individual's age, height, weight, BMI, blood pressure, resting pulse, medical history, mental health status, sex, race, ethnicity, diet, or other risk factors such as smoking, drug or alcohol abuse or any health status metric disclosed herein. The information communicated may further include answers from the individual to a medical professional's questions. The questions may or may not be health-related. The medical professional may ask a subject or others in the vicinity of a subject to check the subject's health status by using the device. During the communication, a medical professional may provide one or more instructions to the subject or others in the vicinity of the subject. The one or more instructions may comprise, but not limited to, asking the subject to take a medication, informing the subject when to take the medication, asking the subject to perform, continue or stop an action, informing service providers to provide certain medical assistance to the individual, requesting the subject eat, take or administer a certain kind of food, or medication.

The patient-side device may not be placed in a residence or a transportation system. The patient-side device may be placed in a public location. The public location may be, but not limited to, a school, company, government agency, shopping mall, movie theater, garden, museum, gallery, food court, outlet, bar, club, zoo, garden, park, gas station, convenient store, grocery store or other areas accessible to the general public. A school mentioned herein may be a kindergarten, element school, middle school, high school, college, graduate school, or professional school.

The patient-side device may enable the communication between an individual in the public location and medical professionals who may or may not be in the public location. The individual in the public location may be a subject in need of medical care. The individual may be a student of a school. The individual may be a service provider working at the public location. The individual may also be a subject not in need of medical care. The communication may be a wireless connection. The wireless connection may include a Wi-Fi receiver, a means for accessing a mobile data standard such as a 3G or 4G LTE data signal, or a Bluetooth receiver. The communication may comprise any information related to the individual. The communication may comprise any information related to the subject's health. The communication may be in the form of text, image, video or voice. The information may include the individual's age, height, weight, BMI, blood pressure, resting pulse, medical history, mental health status, sex, race, ethnicity, diet, or other risk factors such as smoking, drug or alcohol abuse or any health metric described herein. The information may include the subject's health status measure by the device or an apparatus operatively coupled with the patient-side device. The information may further include the answers from the subject to the medical professional's questions. The questions may or may not be health-related. During the communication, the medical professional may provide one or more instructions to the subject. The one or more instructions may comprise, but not limited to, asking the subject to take a medication, informing the individual when to take the medication, informing the service providers to provide certain medical assistance to the individual, or requesting the subject to eat certain kinds of food.

The patient-side device may comprise one or more drawers. Each of the drawers may be assigned to a subject. A given drawer may contain the medications prescribed for a subject who the given drawer is assigned to. The patient-side device may comprise a verification area to verify that the drawer is opened by the correct subject. The patient-side device may comprise one or more apparatus to check a subject's health status and/or measure the subject's physical conditions (e.g., vital signs). The apparatus may be sensors and or medical instruments disclosed herein. The apparatus may be integrated with the patient-side device. The apparatus may also be portable and operatively coupled with the patient-side device.

The patient-side device may be configured to hold one or more medications, vitamins, or supplements. The number of medications, vitamins or supplements held by a patient-side device disclosed herein may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 500 or greater. The medications, vitamins or supplements may be top 70, 100, 150, 200 or 300 medications, vitamins or supplements that are used by public.

Verification

Some embodiments may include a verification area in the patient-side device. The verification area can facilitate visual identification of each item. In the case of pill dispensing, the patient side device can verify a pill prior to dispensing, such as, for instance automated identification or separate confirmation by a medical professional. The verification area can include a camera with an automated visual object recognition module for pills and other items that can be identified by appearance. Some items, for example pills, particularly certain types of generic medications, cannot be easily identified by appearance, so dispensing of these pills and other items can be tracked by the sensors and verified by barcodes associated with the corresponding pill cartridges or other items.

Alternatively, some medications or treatment regimens may require verification by a medical professional or other individual prior to delivery to a patient. For example, an optional verification step can be performed by a nurse practitioner, doctor, or other medical professional, who can view the patient on a video camera installed in an embodiment of the device and observe the patient taking the dispensed medications, especially medications that represent high risk or have high medical importance. Such medical professionals can also use the video camera to verify the medication as it is being delivered to the patient. Some embodiments may be configured for automated verification and visual verification.

The camera can visually record the dispensing of each pill (or plurality of pills), or items dispensed from the device. Such records can be stored on local memory storage devices in a patient-side device, and/or may be transmitted to a remote data storage device, such as through upload via a network to a server computer for archival storage.

In the case of having a pill dispensing feature, some pill cartridges may be loaded into reservoirs for supplemental use in the event they are needed. Such pills can be a low dosage increment so that, for example, upon medical professional authorization, any number of the supplemental pills can be dispensed to a patient, pursuant to the medical professional's instructions. For example, if a diuretic medication such as Lasix (Furosemide) 40 mg is prescribed for a patient on a daily basis (e.g., "1 PO q am"), an embodiment of the patient-side device may include a cartridge of Lasix (Furosemide) 10 mg, so that a medical professional can dynamically add one of the 10 mg pills to the patient's daily dose of 40 mg, to bring the total dose up to 50 mg. As another example, a patient-side device may include one or more cartridges of emergency medication that may be dispensed in the event that a patient's vital signs or other measurement indicate the need for the emergency medication.

Individual medication dispensing features of the patient-side device may be valuable for a number of reasons. For instance, these features may save medications from being discarded when a dosage amount may be changed. Normally, when a patient may have to stop taking a medication at one dosage, the patient may return to a pharmacy and get the same medication at a different dosage. The old medications may then be thrown away. Embodiments of the present invention may reduce the waste of medications because embodiments can deliver supplemental doses that allow previously prescribed medications to be used up. Similarly, medical professionals may monitor a patient's response to medication in or near real-time, and adjust the treatment regimen (or dispense additional medication) through the patient-side device.

Another way of packaging medications may be through a "blister pack" that may contain all of the medications to be taken by a patient at the same time. Typically, the patient may receive a blister pack that contains a plurality of various pills. The blister pack may include a date and/or time printed on the outside (e.g., Monday, Apr. 10, 2016, 8:00 am), among other identifying information and useful information. For example, Blister packs can be barcoded or include an identifier in the same manner as pill cartridges as described herein. The information may instruct the patient on when to ingest the contents. In some embodiments, a vendor can deliver multiple blister packs to the patient (e.g., a week's worth of blister packs), so that a patient may have them in advance. The patient then merely may open the packet and ingests the various pills. Embodiments of the patient-side device can be configured to receive and dispense blister packs from a corresponding pill reservoir, and alternately from a rotating flat carousel. The blister packs can be loaded into each reservoir tray similar to the loading for pill cartridges into pill reservoirs. Alternatively, an entire carousel containing pre-loaded blister packs can be loaded into an embodiment of the invention.

Embodiments of the invention can account for and warn subjects and medical professionals about drug-to-drug interactions between two or more medications. For example, some embodiments may be configured to operate software that performs contraindication checks using existing drug databases. The existing drug databases may include, but not limited to, Adverse Drug Effects Database, AHFS Supplemental File, Allergen Picklist File, Average WAC Pricing File, Brand Probability File, Canadian Drug File v2, Comprehensive Price History, Controlled Substances File, Drug Allergy Cross-Reference File, Drug Application File, Drug Dosing & Administration Database, Drug Image Database v2.0/Drug Imprint Database v2.0, Drug Inactive Date File, Drug Indications Database, Drug Lab Conflict Database, Drug Therapy Monitoring System (DTMS) v2.2/DTMS Consumer Monographs, Duplicate Therapy Database, Federal Government Pricing File, Healthcare Common Procedure Coding System Codes (HCPCS) Database, ICD-10 Mapping Files, Immunization Cross-Reference File, Integrated A to Z Drug Facts Module, Integrated Patient Education, Master Parameters Database, Medi-Span Electronic Drug File (MED-File) v2, Medicaid Rebate File, Medicare Plans File, Medical Condition Picklist File, Medical Conditions Master Database, Medication Order Management Database (MOMD), Parameters to Monitor Database, Patient Safety Programs File, Payment Allowance Limit-Part B (PAL-B) v2.0, Precautions Database, RxNorm Cross-Reference File, Standard Drug Identifiers Database, Substitution Groups File, Supplemental Names File, Uniform System of Classification Cross-Reference File, and Warning Label Database. The software to perform the contraindication may rely on structured computation, for example providing registration, segmentation and other functions, with the centrally-processed output made ready for downstream analysis. The software may rely on unstructured computation, artificial intelligence or deep learning. The contraindication check may be performed by using an internal database. The internal database may be created through gathering the data from the patient-side device, medical professional-side device and/or enterprise device.

To perform a contraindication check, a subject may enter the information related to at least two medications to a patient-side device. The subject may also need to enter other useful information related to the subject who takes the medications. The useful information related to the subject may include, but not limited to, the patient's age, height, weight, BMI, blood pressure, resting pulse, medical history, mental health status, sex, race, ethnicity, diet, or other risk factors such as smoking, other drug regiments, and drug or alcohol abuse. The information related to the medications may include the name, the chemical compound, the producer, the expiration date, the ingredients, and the dosage of the medications. The information may be entered to the patient-side device through texts, images, voice, or videos. The patient-side device may comprise a display screen, a voice detector, a microphone, a smart speaker, and/or an image detector to capture the information. In other embodiments, the device can perform a contraindication check automatically once drug regiment for a subject is programed.

An image detector described herein may be an optical detection apparatus. The optical detection apparatus may optically read or scan a visual element. The image detector may be a camera. The image detector may be configured to be able to capture a visual graphical element, such as a bar code (e.g., one-dimensional, two-dimensional), text, a picture, a sequence thereof, or any other forms of graphical authentication indicia. The image detector may include a hardware and/or software element. The image detector may be a hardware camera sensor operably coupled to the patient-side device. For example, the camera sensor can be embedded in the patient-side. Alternatively, the image detector may be located external to the patient-side, such as connected via cable or wirelessly, and image data of the graphical element may be transmitted to the patient-side device via communication means disclosed herein. The image detector can be controlled by applications and/or software configured to scan a visual graphical code. For example, the camera may be configured to scan a visual graphical code. The camera can be controlled by a processor natively embedded in the patient-side device.

Embodiments of the patient-side device may confirm the identity of the patient. For example, some embodiments of the patient-side device may be configured to perform facial recognition, thumbprint or fingerprint authentication, and retinal authentication of a patient. Some embodiments can combine these methods to employ two-factor or three-factor authentication using any combination of the disclosed authentication methods.

Some embodiments of the patient-side device may include a locked dispensing module physically or wirelessly. For example, a pill-dispensing module can be unlocked physically with a key (for example, to refill the pill reservoirs with pills and/or pill cartridges), or it can be unlocked electronically by an authorized command delivered to an embodiment via a network connection.

Display Screen

Embodiments of the patient-side device may include an information display screen. For example, some embodiments of the patient-side device include a front-facing screen that may include a touch interface. The screen may be a liquid crystal display, similar to a tablet computer. The screen may be accompanied by one or more speakers, and may be configured for providing visual and audial instructions to a subject. In a demonstrative interaction, an avatar on the display screen may correspond to a user. The avatar may initiate an interaction with a patient by stating, for example, "Good morning, Mr. Smith, you have 5 medications today; please touch the green 'go' sign to begin," via a speech generation device, such as a speaker.

In some cases, a touch screen display can be an 8 inch capacitive high-resolution display. In some embodiments, a touch screen comprises a color screen. In some instances, a touch screen can have a resolution of at least or about 800×600. In some cases, a touch screen can allow for multi-touch gestures. A touch screen can allow for calibration and/or correct for differences in finger size. Furthermore, a touch screen can allow for usage while wearing a glove (e.g. latex surgical glove). In some instances, a power button can be integrated into a touch screen. In some instances, a power button can be separate from a touch screen.

Peripheral Device

A peripheral device can be connected to the patient-side device via known methods of connection, such as, for example, a tether that may be attached to the peripheral on one end and attached to the patient-side device via a hook (or similar attachment point) near one or more of the ports. For safety reasons (e.g., the patient tripping over wires), certain peripheral devices, such as digital scales, may connect to the patient-side device wirelessly, in lieu of wired connections.

Some embodiments may include movable doors over one or more peripheral device ports. During operation, a user may open a door, and the peripheral device behind the door may be extended outward to the user, or alternatively the user can reach into the bay to retrieve the peripheral device. The vital sign peripheral may remain tethered to the health management device so the patient cannot misplace them, for example. Each bay door and each bay may be a different size, to accommodate a specific vital sign peripheral.

In some embodiments, the peripheral device and door may be remotely operated by a third party, such as a medical professional. For example, a medical professional operating a retraction mechanism remotely can retract one or more peripheral devices into its corresponding storage bay upon completion of a data collection process. If a patient does not need one or more measurements, they may not be included with the patient-side device. Thus, the specific complement of peripheral devices can be customized depending on what that patient or treatment regimen requires. In other embodiments, a peripheral device can be turned on/off remotely by a medical profession.

In some embodiments, peripheral devices may communicate with the patient-side device via Bluetooth or an equivalent wireless network protocol. Peripheral devices can also communicate with the patient-side device via known hardline communications protocol, such as USB, RS-232, TCP/IP, or other similar protocols known in the art. Embodiments of the patient-side device can be configured to interface with connected peripheral devices either serially or in parallel. Some vital sign peripherals may be installed outside the embodiments and plugged into the embodiments for data collection and analysis.

A device provided herein can be configured for connection to one or more peripheral devices. A peripheral device can be, e.g., a monitor, printer, computer, tablet, smartphone, other spirometer, fax machine, etc. A peripheral device can be connected to a device provided herein by any means of connections described herein. In some embodiments, a device provided herein can interface with one or more peripheral devices. In some embodiments, a peripheral device can include health (e.g., medical) sensors/devices and or environmental sensors/devices. For example, health sensors can include a blood pressure meter, pulse meter, scale, thermometer, glucometer, oxymeter, and other similar devices and or sensors. Environmental sensors/devices can include smoke detectors, CO detectors, and temperature sensors. In some embodiments, a peripheral device can comprise a video capture device, a kinematic orientation/motion tracker, an accelerometer, a gyroscope, an attitude sensor, a global positioning system, a temperature monitor, a blood pressure monitor, a biometric security device, an electrocardiography (EKG/ECG) sensor, or an electroencephalography (EEG) sensor. In some aspects, a ECG can be a 12-lead ECG.

Data Collection and Configuration

Embodiments of the patient-side device may be configured to collect data based on the desired data collection schedule. Thus, a medical professional may determine the schedule upon which a subject's vital signs and other measurements should be taken. For example, embodiments of the patient-side device can collect vital sign data from a patient at least once every day, or within a certain time after a patient ingests a pill. The vital sign data can be uploaded to a server immediately or on a periodic basis, and may be configured to alert a medical professional or other third party in the event of a measurement indicating an emergency or other scenario meriting a warning.

Some embodiments of the patient-side device may collect and anonymize data for mass analysis. Similarly, systems of patient-side devices may be configured to support mass analysis. The value of such data may not just in the quantity, but also in the fact that longitudinal data profiles can be generated, and that there may be a direct link in the data to patient behavior. It may be appreciated that embodiments can be tailored to provide customized analytics that build on longitudinal data. Similarly, some embodiments can be given the ability to intervene with respect to behavior modifications.

In other embodiments, a device disclosed herein can measure, a blood pressure measurement of the subject, a blood glucose level of the subject, a blood oxygen level of the subject, a blood glucose level of the subject, or a sinus rhythm of the subject. The sinus rhythm is a normal sinus rhythm, sinus tachycardia, sinus bradycardia, atrial fibrillation, atrial flutter, ventricular tachycardia, or a ventricular fibrillation. A device disclosed herein can use a measurement to change or adjust a medication dispensing schedule, the medication to be taken, or a dosage of the medication. In some instances, a measurement from a peripheral device can be compared to a reference value or range. A device disclosed herein can use a measurement to change or adjust a medication dispensing schedule, the medication to be taken, or a dosage of the medication based on if a measurement is within or outside a predetermined range.

Take pharmaceutical research as an example. With respect to large-scale studies, embodiments may be configured to produce data covering populations, measurements, and periods of time, in a way that has not been possible in the past. Similarly, embodiments may be configured to record when each patient ingested a particular medication, the patient's vital signs or other measurements, and document such data for subsequent verification.

Embodiments of the patient-side device may take numerous forms other than as shown in the specific embodiments described herein. For example, some embodiments may take the form of a "thin client" connected to the Internet or other network by any one of several known means (e.g., cellular, WIFI, cable, Ethernet, etc.). Here, "thin client" may mean that all collected data will be uploaded to a server via the Internet as soon as practicable. Collected data can be stored temporarily in the memory of the patient-side device, but to minimize the risk of data loss, the data can be uploaded whenever possible.

Embodiments can support a variety of protocols for connecting to the Internet. If, for example, a wireless network goes down but a cable system may be operational, embodiments may be able to reconfigure its network connection to use the cable system. The same can occur with respect to using a cellular network or any other means of connecting to the Internet. Embodiments of the patient-side device can support a video camera, a screen or monitor that may be capable of displaying video images as well as computer-generated text, graphics, and images.

When connected to the Internet, embodiments of the patient-side device can support a variety of protocols for data transfer, including but not limited to TCP/IP and FTP. Embodiments can also support interactive telephone calls and video calls (e.g., Skype, FaceTime, etc.).

EXEMPLARS

FIG. 1 is an exemplar embodiment of a patient-side device 1001. Device 1001 may include an information display 1003, that in some embodiments may be responsive to touch or other devices. Speakers 1005 may work in conjunction with display 1003 to provide information, guidance, and instructions, for example, to a user (e.g., patient, caretaker). Device 1001 may include one or more ports 1009 for interfacing with peripheral devices. Display 1003 may also be configured to receive input from a user, such as responses to questions, and use of one or more peripheral devices. Device 1001 may include one or more extendible trays 1011, to dispense one or more medications contained in device housing 1013. Some embodiments may include a camera 1007 to capture images or video of the user, and the device 1001 may be configured to provide live video interaction between a user and a third party, such as a medical professional.

Figure 2:
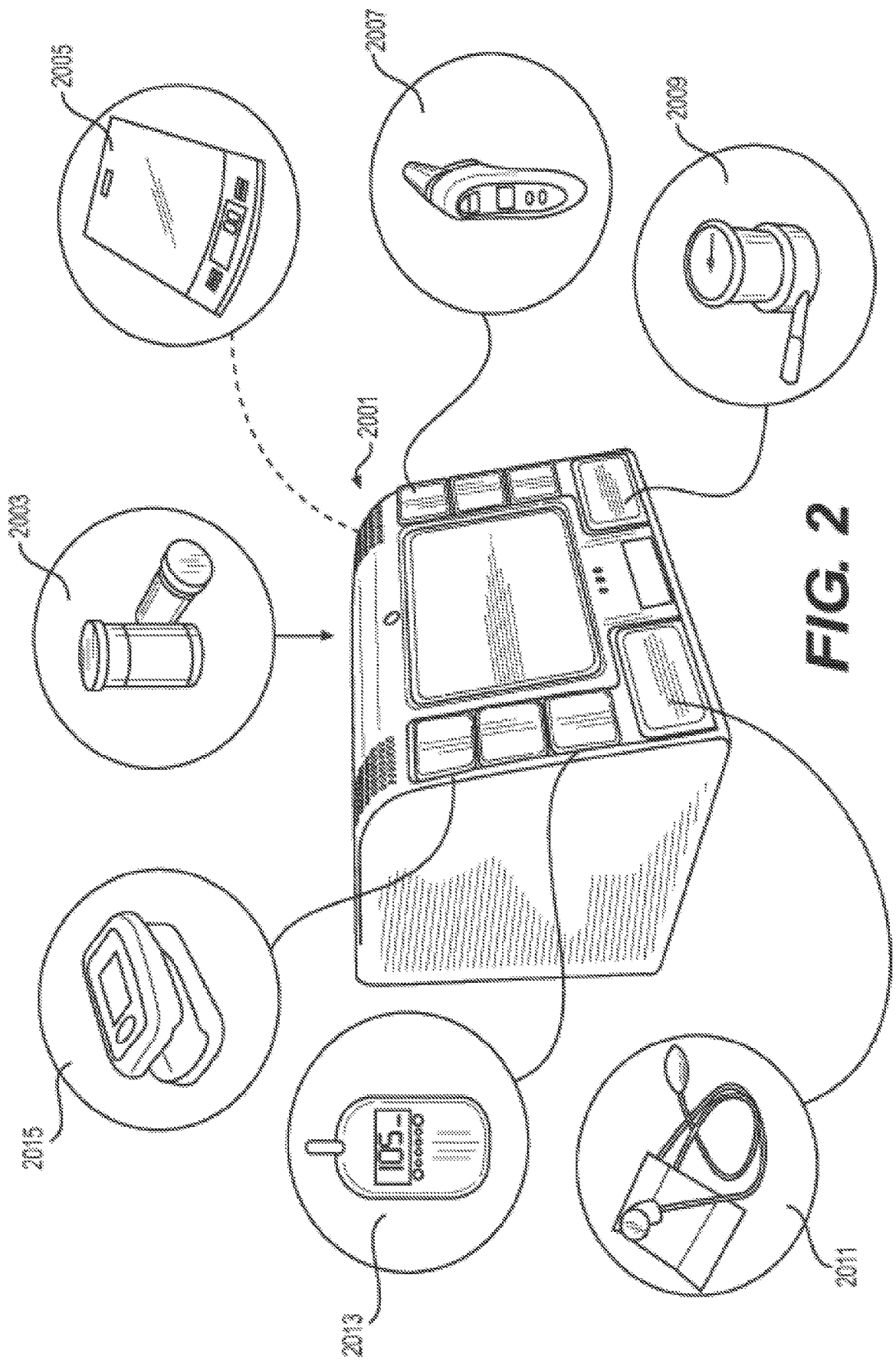
FIG. 2 is an exemplar embodiment of a patient-side device connected to multiple peripheral devices.

FIG. 2 is an exemplar embodiment of a patient-side device 2001 connected to multiple peripheral devices. Device 2001 may be configured to dispense pills 2003 as described here. Further, it may be appreciated that device 2001 may be connected to and interface with numerous peripheral devices. For example, a device 2001 may connect to peripheral devices such as a digital scale 2005, a thermometer 2007, a spirometer 2009, blood pressure measurement devices 2011, a glucose monitor 2013, pulse oximeter 2015, and the like. The device 2001 may be pre-programmed for interfacing with one or more peripheral devices, and seamlessly receive, analyze, and report patient data to one or more medical professionals. Some embodiments may include one or more universal ports, and may connect with a new peripheral device. Upon connecting, the device 2001 may search for and download operating software and drivers for the new peripheral device.

Figure 3:
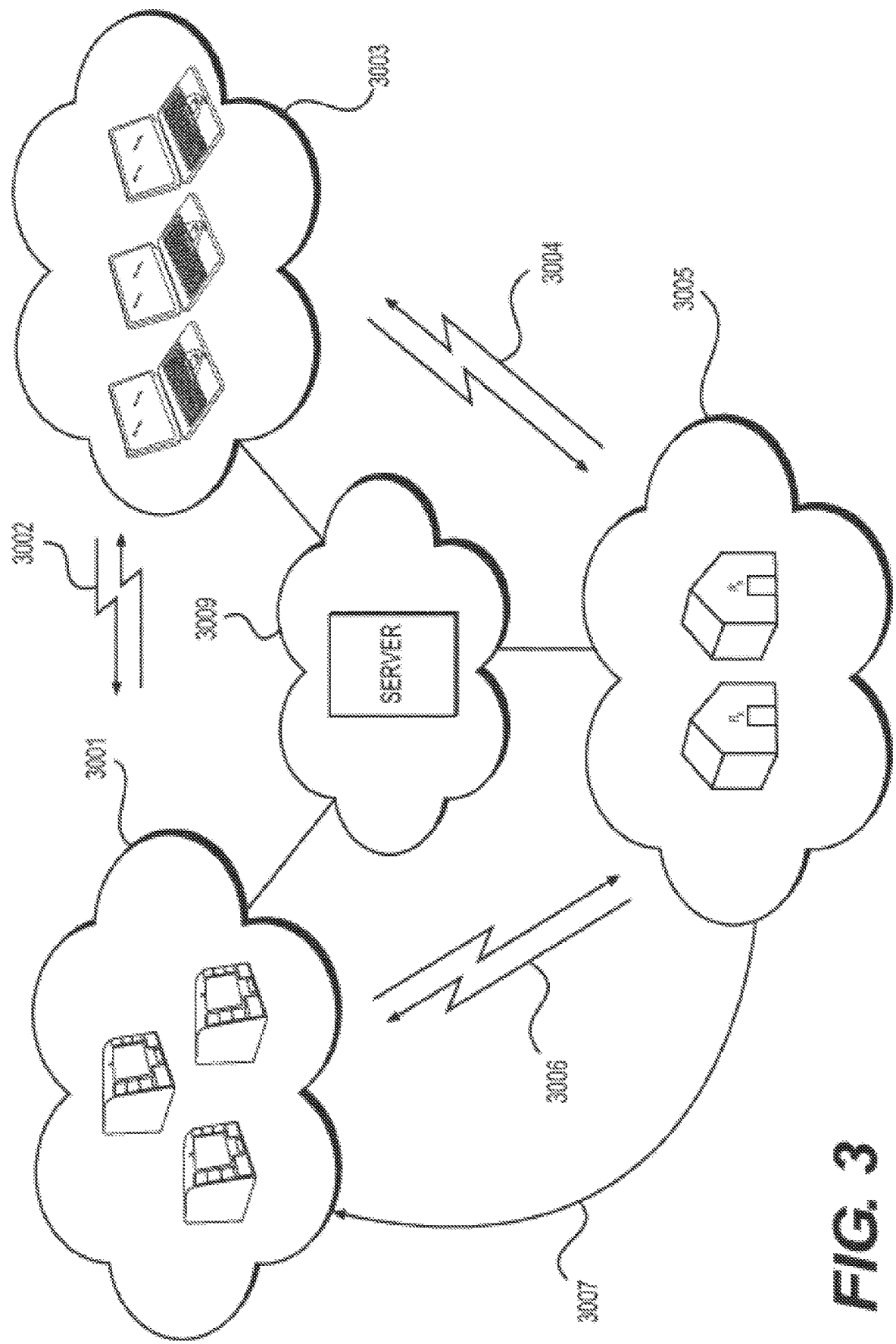
FIG. 3 shows a system for remote dispensing medications and monitoring patient status.

FIG. 3 shows a system for remote dispensing medications and monitoring patient status. The system may include a plurality of patient-side devices 3001. The patient-side devices may be installed at, for example, patients' homes, throughout a hospital, among other possible sites, and may be connected to the Internet or a network. Patient-side devices 3001 may be in communication with medical professionals 3003, which may include treating physicians, registered nurses, and the like, operating computing devices in communication with patient-side devices 3001. Communication 3002 between patient-side devices 3001 and medical professionals 3003 may involve the exchange of data as described herein, including, for example, medication treatment regimens and instructions to the patient or caretaker, measurement and monitoring of patent vital signs and other data, analysis of data, video and/or voice conferencing, and the like. Depending on the implementation, medical professionals 3003 may include professionals other than treating medical specialists, such as research scientists and analysts.

The system may also include one or more pharmacies 3005, configured to receive prescription and regimen information from medical professionals 3003 through communications 3004. Pharmacies 3005 may prepare pill cartridges and/or blister packs for shipment 3007 to a patient or caretaker. Depending on the embodiment, a pharmacy 3005 or a medical professional 3003 may provide the identifier on a cartridge or blister pack for a patient-side device to read. Although some embodiments include data on the cartridge or blister pack for a patient-side device to read and determine the instructions, in some embodiments the pharmacy may send such data to a patient-side device through data communication 3006. Additionally, the medical professional 3003 may send such instructions and data to the patient-side device, at or near the time the medical professional 3003 sends a prescription to the pharmacy 3005.

In some embodiments, the system may include one or more servers 3009. Server 3009 may be a central server for an entire system, or may be specific to a particular network, medical professional, or pharmacy. For example, a pharmaceutical research company may maintain a central server in connection with clinical trials, whereas a network of healthcare professionals may maintain separate servers. The server(s) 3009 may be used for multiple purposes, and the present approach should not be limited to the specific purposes described herein. For example, server(s) 3009 may retain data generated by patient-side devices 3001, and/or store data generated by and/or provided to medical professionals 3003 and pharmacies 3005. In some embodiments, server(s) 3009 may support communications between parties, such as video and voice conferencing between patients and medical professionals. In some embodiments, server(s) 3009 may perform data anonymizing and analyzing services.

Although there may be numerous potential applications for the present approach, demonstrative use cases with respect to various embodiments may include: (1) post-acute care; (2) chronic conditions; and (3) clinical trials. Post-acute care use cases may include, for example, post cardiac surgery or other serious surgical procedure such as hip or knee replacement operations; post-hospital diabetes complications, out-patient care; and hospital-acquired infections, for example pulmonary infections. Chronic use cases may include, for example: complex polypharmacies, diabetes, Coumadin management, asthma, sleep apnea, mental health, Alzheimer's, mild cognition impairment and out-patient care. Clinical trial enablement platform use cases may include, for example: electronic data capture in-home, the ability to adjust medication, ability to deliver and conduct clinical trials in rural and remote communities, etc.

A fourth category may include recreational sports and health applications. This category may apply to athletes and fitness buffs, who wish to keep track of supplements such as vitamins, minerals, and other preparations, as well as to record and analyze various vital signs that relate to athletic performance. Embodiments of the present approach can provide users with an ability to manage a health portfolio with all supplements, vital sign measurements, and other related data, all linked together in the same device. For example, embodiments of the patient-side device may be configured to collect data from personal data collection devices such as a wearable device like a Fitbit as part of an in integrated wellness program. Embodiments can then export all pill dispense data and vital sign data in a variety of spreadsheet formats (e.g., Excel), among other useful formats. Embodiments of the invention can provide real-time data analysis tools that can identify weaknesses, and can compare collected data to statistical data corresponding to various categories of individuals in a population. Embodiments can determine if a certain vital sign measurement may be changing over time and can report that change to the patient or to medical professionals. When that change in a vital sign represents a potential problem, embodiments can then, for example, enable a video conference call with different callers: nurse, patient, family member, or doctor, for example. Stakeholders can participate and watch the patient. They can perform remote evaluations and coordinate scheduling of a doctor's visit if necessary. The functionalities disclosed herein can be use by those having access to a patient-side device disclosed herein.

Medical professionals, including treating physicians, doctors, doctor's offices, registered nurses, clinical trial supervisors, and the like, may have a medical professional-side device configured to, among other things, communicate with patient-side devices and users, receive patient data, and the like. Patient data can be uploaded to the medical professional's system, which in turn can upload the patient data into an EMR (electronic medical record). Nurses can have the same kind of patient-like system as well, so the nurse can demonstrate how to use vital sign devices to a patient who can watch the nurse on the video screen. Doctors and nurses can also have a digital dashboard that can show a history of a patient's vital sign data and drug dispenses. The medical professional-side device may take the form of a software application, user interface, or App, installed on an electronic device. The device can be a portable electronic device.

Additionally, data monitoring protocols can be designed and implemented both at the patient-side device level and at the medical professional-side device or other server. For example, embodiments of the present approach can use a national or average set of protocols (by age, sex, fitness, etc.), or a doctor can set a customized protocol (alarms for various vital signs, for example) for a specific patient.

Embodiments of the patient-side device may include a microprocessor or computer, which controls and/or monitors all or a part of the device's pill loading operations, pill dispensing operations, vital sign data collection, video interaction, prescription management (including doctor-authorized edits and updates), and data uploading operations. Access to embodiments of the patient-side device may be controlled by various security protocols as may be known in the art. For example, medical professional access to and control of a patient-side device may be limited or controlled, as may be access by any other medical professionals and even the patients.

Embodiments may include internal power storage devices. Additionally, an external battery can supply power to embodiments of the patient-side device. The use of an external battery can help to keep the temperature of the medications stable, whereas an internal power storage device may require additional heat sinking features. An external battery can also help to provide power to the embodiments in the event of a failure or spike in external power sources.

Figure 4:
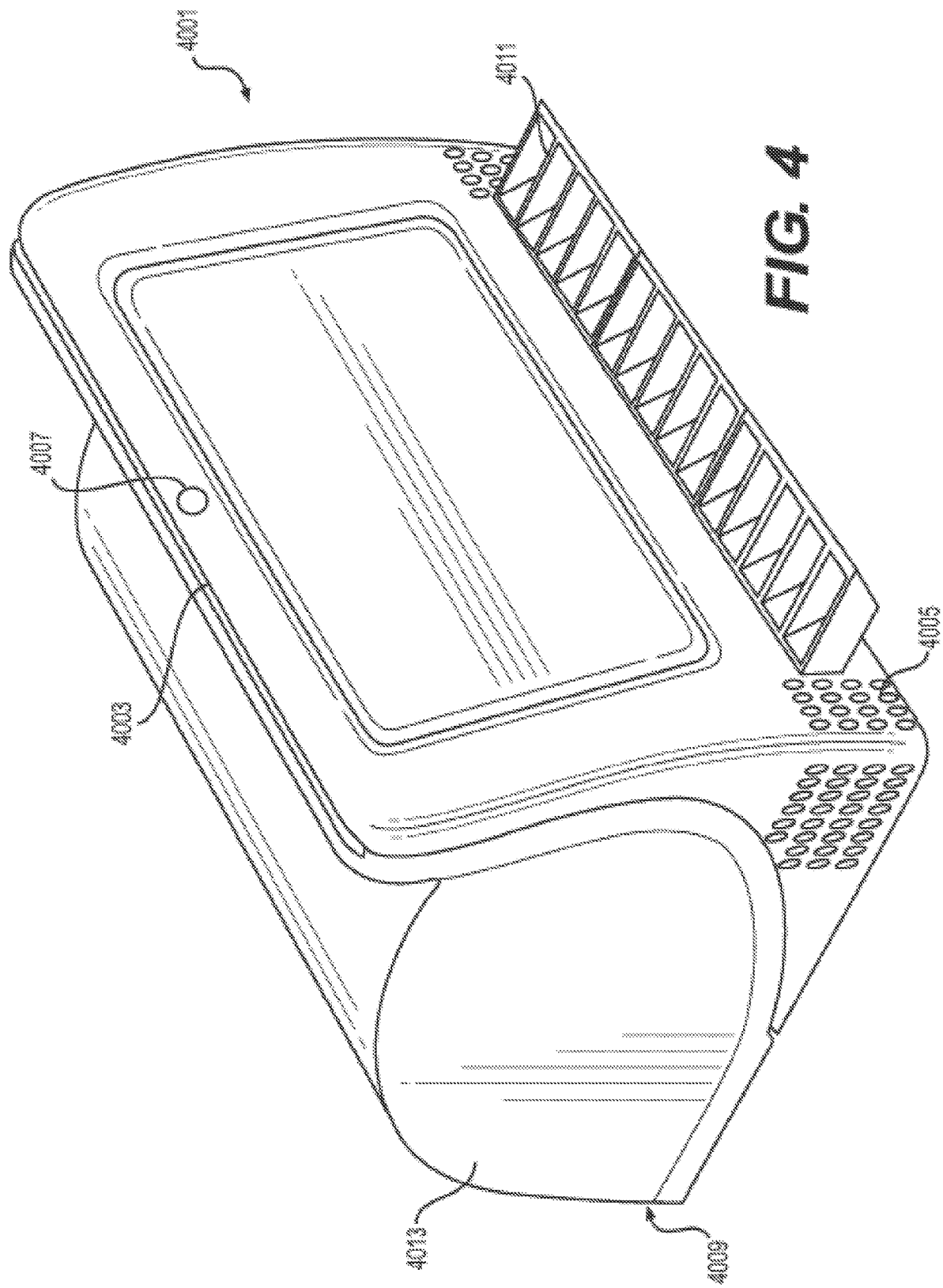
FIG. 4 illustrates another embodiment of a patient-side device.
Figure 5:
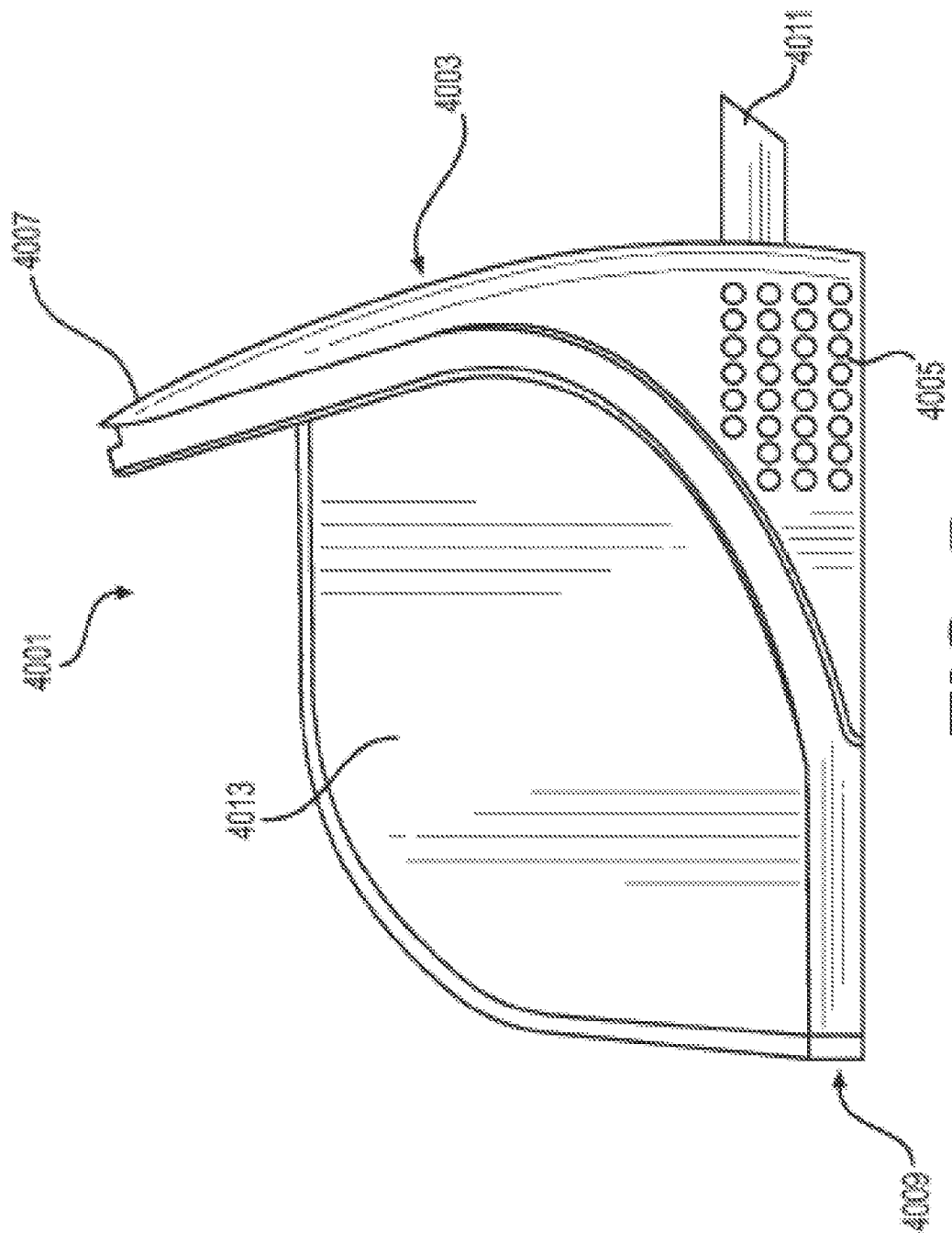
FIGS. 5-7 show side, top, and front views, respectively, of an embodiment of a patient-side device.
Figure 6:
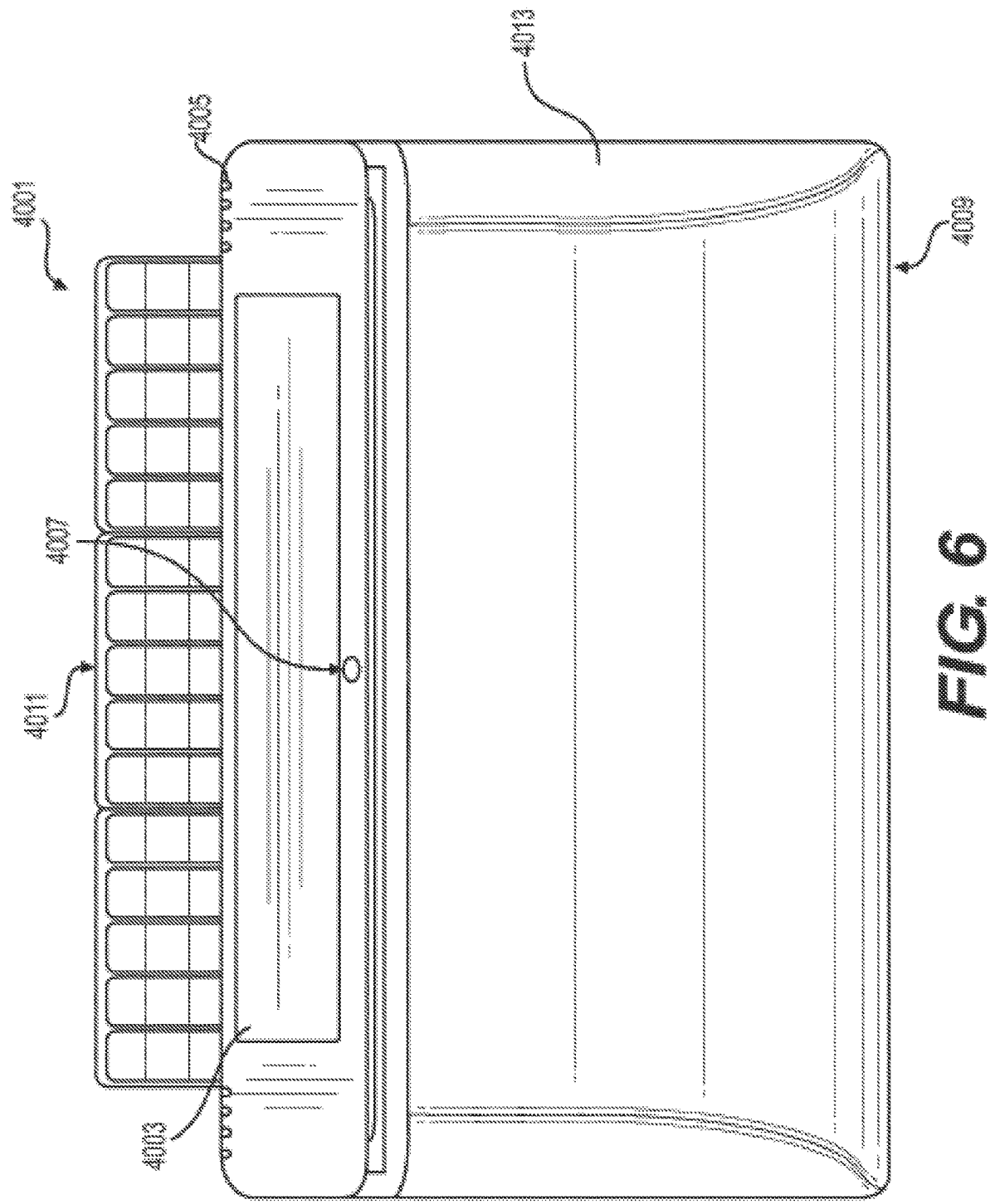
Figure 7:
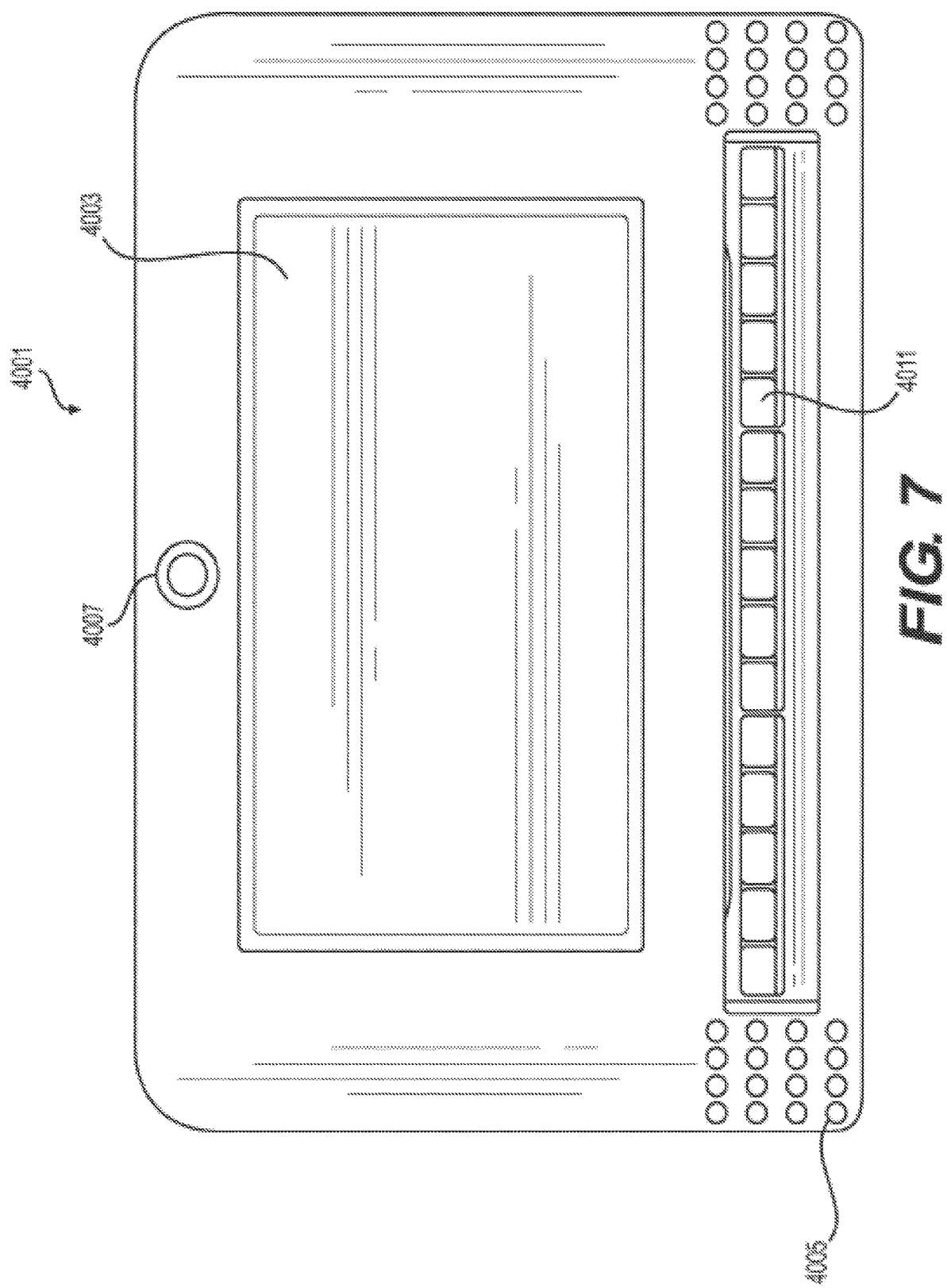

FIG. 4 illustrates another embodiment of a patient-side device 4001, and FIGS. 5-7 show side, top, and front views, respectively, of an embodiment of the same embodiment. Device 4001 may include an information display screen 4003 that may be touch-sensitive and/or responsive to devices such as stylus pens and the like. Device 4001 may include one or more speakers 4005 with or without a microphone, to enable audio communications between a user (e.g., a patient or caretaker) and a medical professional, as well as to enable the device 4001 to provide instructions to the user and/or other interactions (e.g., questioning, peripheral device usage, etc.). Device 4001 may include an external camera 4007 to take images or video of the user, such as to support video conferencing or to confirm or record the identity of the user. Some embodiments may include one or more ports 4009 for connection to and interfacing with peripheral devices, as discussed above. Device 4001 may include one or more extendible trays 4011, to receive one or more pills dispensed from inside device housing 4013, and provide the pills to the user. Extendible trays 4011 may include disposable tray liners (not shown). The patient-side devices may vary significantly in appearance, design, and the like, and that the present approach may not be not intended to be limited to the embodiments disclosed herein.

Figure 8:
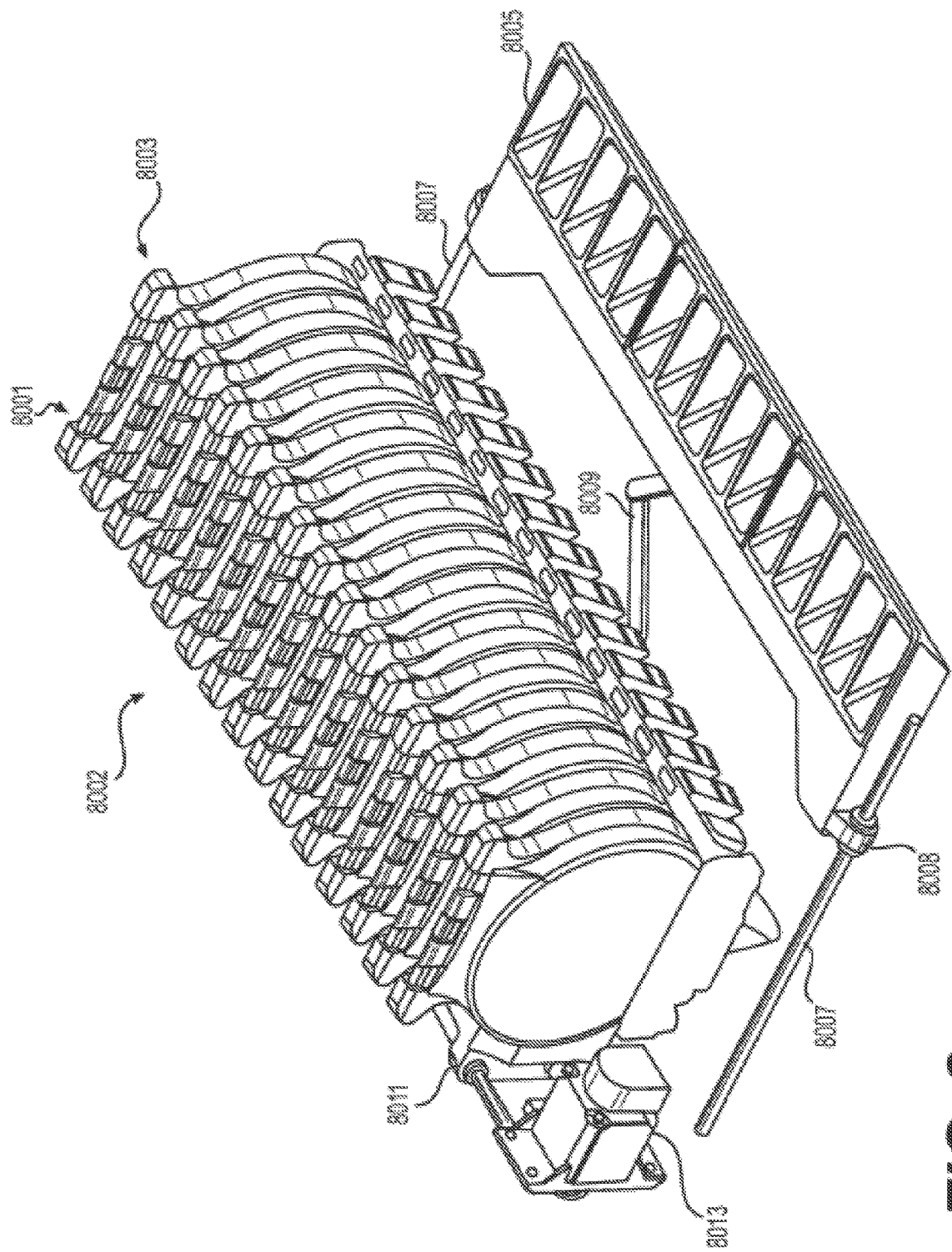
FIG. 8 depicts an embodiment of a cartridge and tray assembly of a patient-side device.

Embodiments of the patient-side device may incorporate various mechanisms for verifying and dispensing medications. FIG. 8 depicts an embodiment of a cartridge and tray assembly 8001 of a patient-side device, as may be located inside a device housing and not readily accessible (in some embodiments). Assembly 8001 may include a medication dispenser bank 8002, having one or more reservoirs configured to receive one or more medication cartridges 8003. The other embodiments may include pre-loaded pills in a reservoir, or be configured for use with a blister pack or other pill source. Pills from one or more medication cartridges 8003 may be selectively dispensed into extendible tray 8005, which may then extend to outside of the device housing (not shown) and permit a user to retrieve the pills. In some embodiments, tray 8005 may not extend until after one or more pill dispensing verification features have been completed.

Tray 8005 may include one or more guide rod bores 8008 to receive guide rods 8007. Extension mechanism 8009 may operate to extend and retract tray 8005 pursuant to one or more algorithms. Assembly 8001 may include a belt drive assembly 8011, which may allow pill indexing sensor to travel along a row of cartridges 8003, read information present on one or more identifiers (not visible in this drawing), and dispense pills pursuant to instructions present on local device memory, received from a medical professional-side device, and/or present in the information on the cartridges. In this embodiment, drive assembly 8011 may operate similar to a Dot matrix printer head, moving back and forth along the row of cartridges 8003 as needed. Alternative drive mechanisms may be used if the array of reservoirs and/or cartridges may be not linear or contains more than one row.

FIG. 9 shows a medication dispenser cartridge 9001 according to an embodiment of the present approach. In this embodiment, cartridge 9001 may include a central pill control gear 9005 that defines a plurality of pill slots 9003 around the gear teeth. In this particular embodiment, slots 9003 may be circumferentially arranged around the central hub of control gear 9003. Gear 9003 may be mechanically engaged to indexing drive gear 9007, such that when indexing drive gear 9007 rotates, pill control gear 9005 rotates. After sufficient rotation, a pill slot 9003 may align with dispensing chute 9009. Any contents in the pill slot 9003 aligned over chute 9009 then may fall from the slot and proceed along a verification and/or dispensing pathway.

Cartridges may take a number of different forms, and may include various measures to prevent tampering. In this embodiment, cartridge 9001 may include a cover 9011 that may, in some variations, be transparent. Cover 9011 may connect to the cartridge body at hinge 9012, thereby permitting cover 9011 to be opened, and exposure of the pill slots 9003. To prevent tampering, cartridge 9001 may include one or more locking mechanisms 9013 configured to prevent cover 9011 from easily opening. Locking mechanism 9013 may correspond with a separate device (not shown) to unlock the locking mechanism, to permit refilling the cartridge. Additionally, cartridge 9001 may include a pair of handles 9015 to facilitate easy handling and loading into a patient-side device's reservoir (not shown in this drawing).

Figure 11:
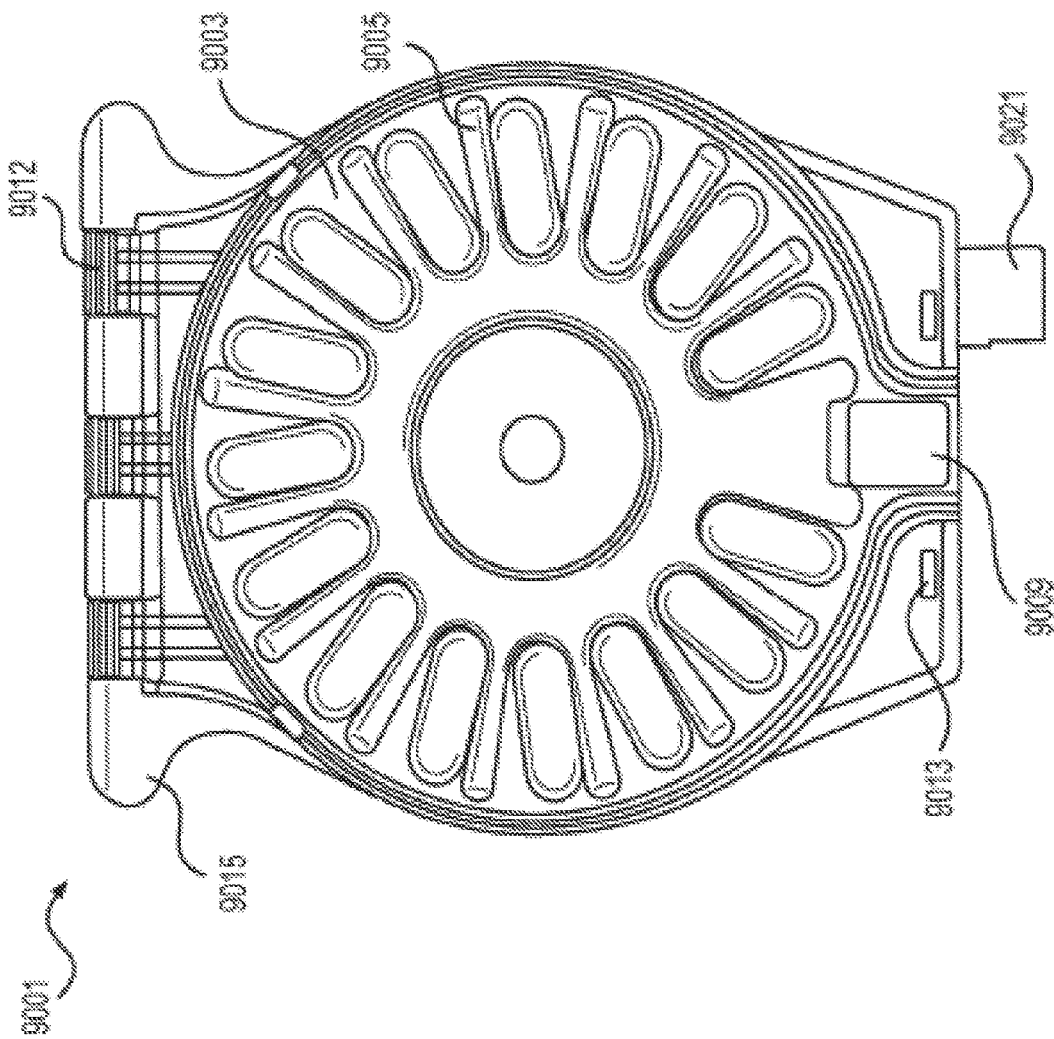
FIGS. 10 and 11 illustrate side and top views, respectively, of a medication dispenser cartridge according to an embodiment of the present approach.
Figure 10:
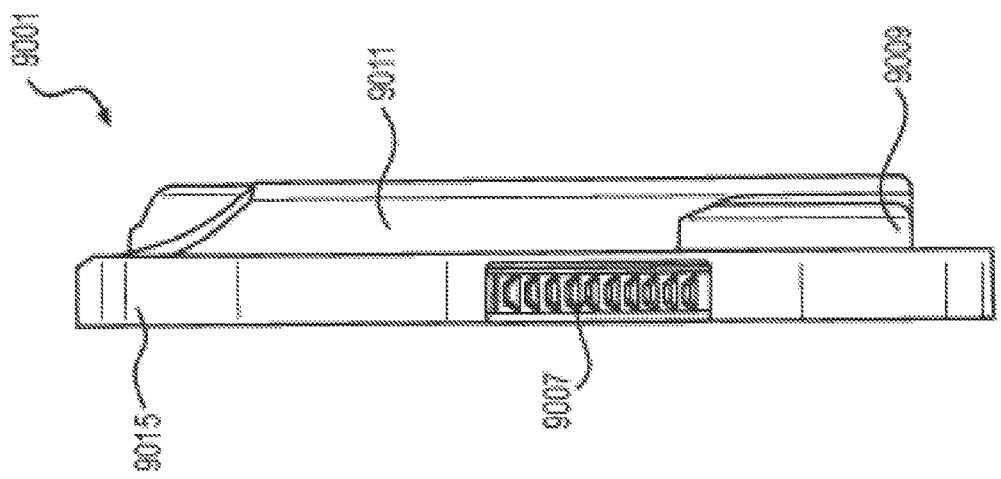

FIGS. 10 and 11 illustrate side and top views, respectively, of a medication dispenser cartridge according to an embodiment of the present approach. In addition to the features discussed with respect to FIG. 9, cartridge identifier 9021 may be visible in these drawings. The cartridge identifier 9021 may include various information to identify the cartridge, its contents (e.g., pills), the source of the cartridge and/or contents, information about the prescription and/or treatment regimen, instructions for the patient or caretaker, and the like. Cartridge identifier 9021 may include both visible information and computer-readable information, such as a barcode or other symbology that a pill indexing sensor can read and interpret. In some embodiments, the identifier may have more than one surface, and different information may be made available on different surfaces. For example, a computer-readable code may be on one surface of the identifier, and human-readable information may be available on an opposing surface.

Figure 12:
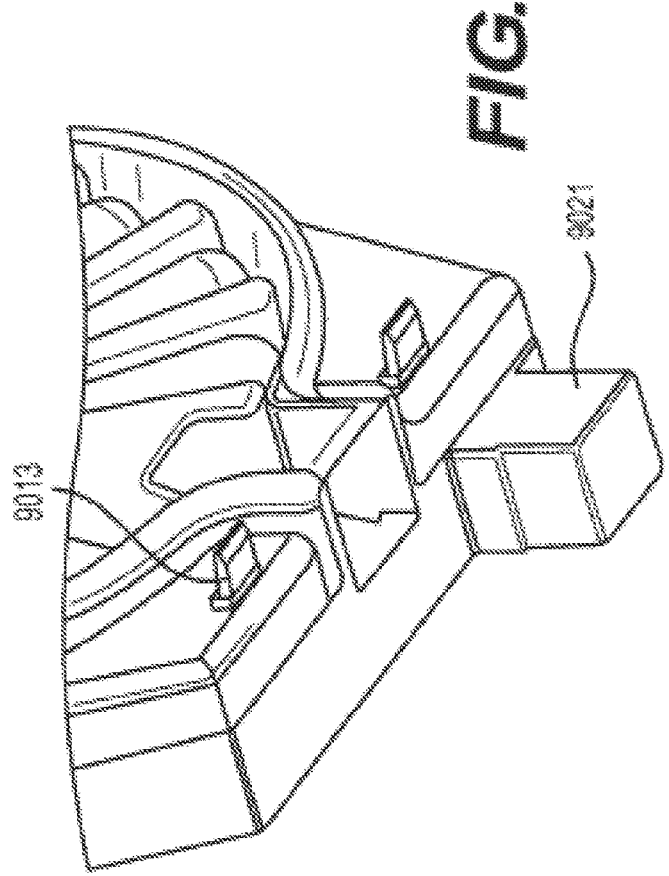
FIG. 12 shows an up-close view of a portion of side and top views, respectively, of a medication dispenser cartridge according to an embodiment of the present approach.

FIG. 12 shows an up-close view of a portion of side and top views, respectively, of a medication dispenser cartridge according to an embodiment of the present approach. This view may show locking mechanisms 9013 protruding from the cartridge frame and extending through a corresponding slot in cover 9011. Cartridge identifier 9021 may protrude below the chute 9009, such that it may be visible beneath the reservoir. As discussed below, embodiments may include one or more sensor devices configured to scan the identifier 9021 for contents, instructions, and the like. The position of identifier 9021 may vary in other embodiments, depending on factors such as the layout and configuration of the reservoirs, the shape and placement of cartridges, and the path of the drive assembly.

Figure 13:
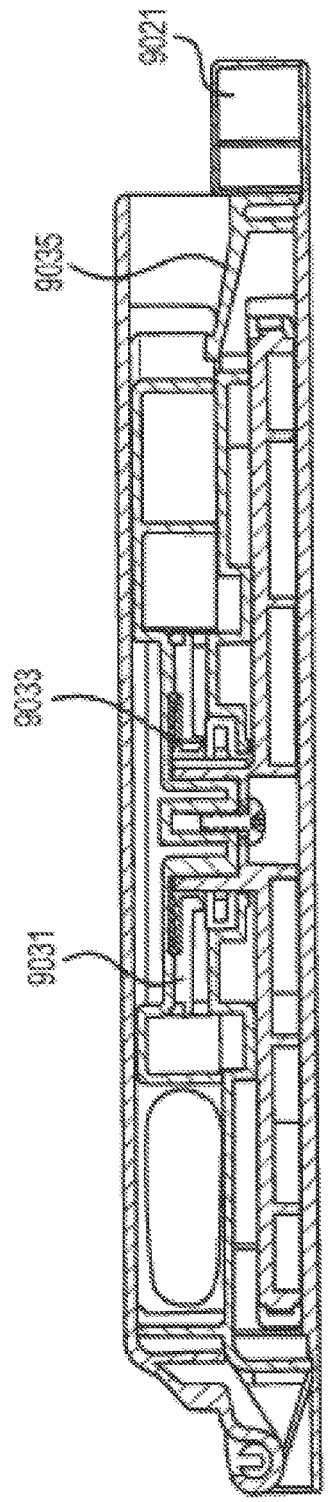
FIG. 13 shows a cross-sectional view of an embodiment of a medication dispenser cartridge, taken along a centerline such that the left-most element of the drawing is the top of the cartridge, and the right-most element is the bottom of the drawing.

FIG. 13 shows a cross-sectional of an embodiment of a medication dispenser cartridge, taken along a centerline such that the left-most element of the drawing may be the top of the cartridge, and the right-most element may be the bottom of the drawing. In this cutaway view, a ratcheting toothed clutch 9031 may be visible. The clutch 9031 may prevent rewind of the cartridge, or intended movement of the pill control gear 9005. Also, the cartridge may include one or more wave springs 9003 to support operation of clutch 9031. Alternative configurations may be possible, and will vary depending on the desired mechanical operation of the cartridge. In this view, locking mechanism 9035 may be also present. A number of mechanisms may be used to secure cover 9011 in the desired position.

Figure 14:
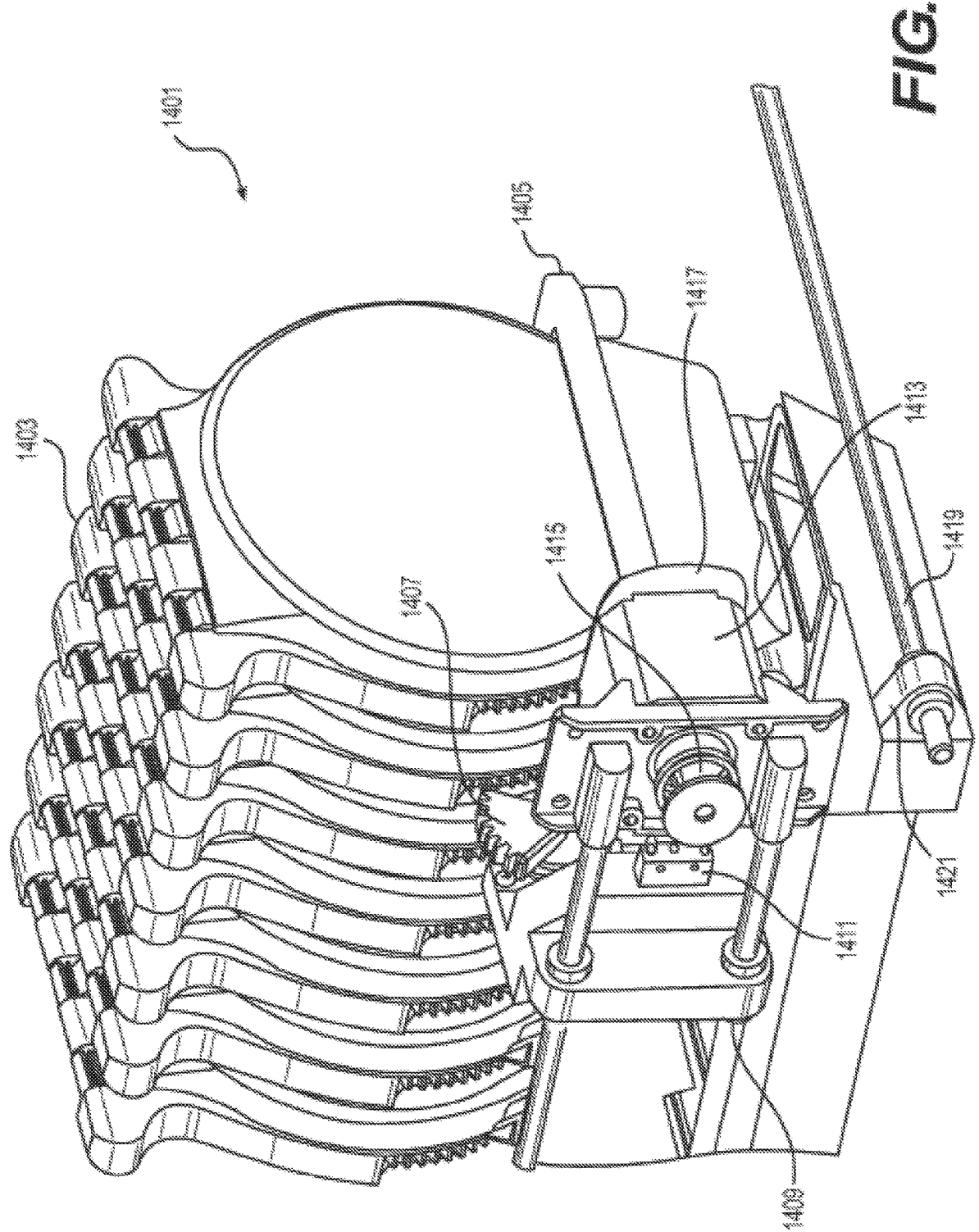
FIG. 14 illustrates the mechanical operation of a cartridge and tray assembly of a patient-side device, according to one embodiment of the present approach.

FIG. 14 illustrates the mechanical operation of a cartridge and tray assembly 1401 of a patient-side device, according to one embodiment of the present approach. A plurality of cartridges 1403 may be inserted into corresponding slots in reservoir 1405. Drive gear 1407 may be configured to engage the indexing drive gear of a cartridge 1403, and operate the pill control gear 9003 as appropriate. Drive gear 1407 may be supported on a pair of linear bearings 1409, such that it may travel from one cartridge to the next as stepper motor 1413 moves the drive gear 1407 mechanism along the row of cartridges 1403 using drive pulley 1415 in connection with a timing belt (not shown). Drive gear 1407 may be disengaged from a pill control gear for movement between cartridges, and engaged to the pill control gear for a subsequent cartridge. Some embodiments may include an optical encoder 1417 (or other sensor) for precisely determining the position of the stepper motor 1413 and drive gear 1407 along the linear bearings 1409, relative to each cartridge 1403. For example, optical encoder 1417 (or other sensor) may be configured to identify various surfaces along the row of cartridges 1403. Alternatively, the cartridges 1403 or reservoir 1405 may include various markings for the optical encoder 1417 (or other sensor) to read and determine the position relative to the rest of the assembly 1401. Some embodiments may include a limit switch 1411 to reset the position of the drive gear 1407 and motor 1415 assembly, such as during cartridge replacement events. Guide rods 1419 may connect to or protrude from guide rod bearing 1421. As discussed above, the tray may extend outward along guide rods 1419.

Figure 15:
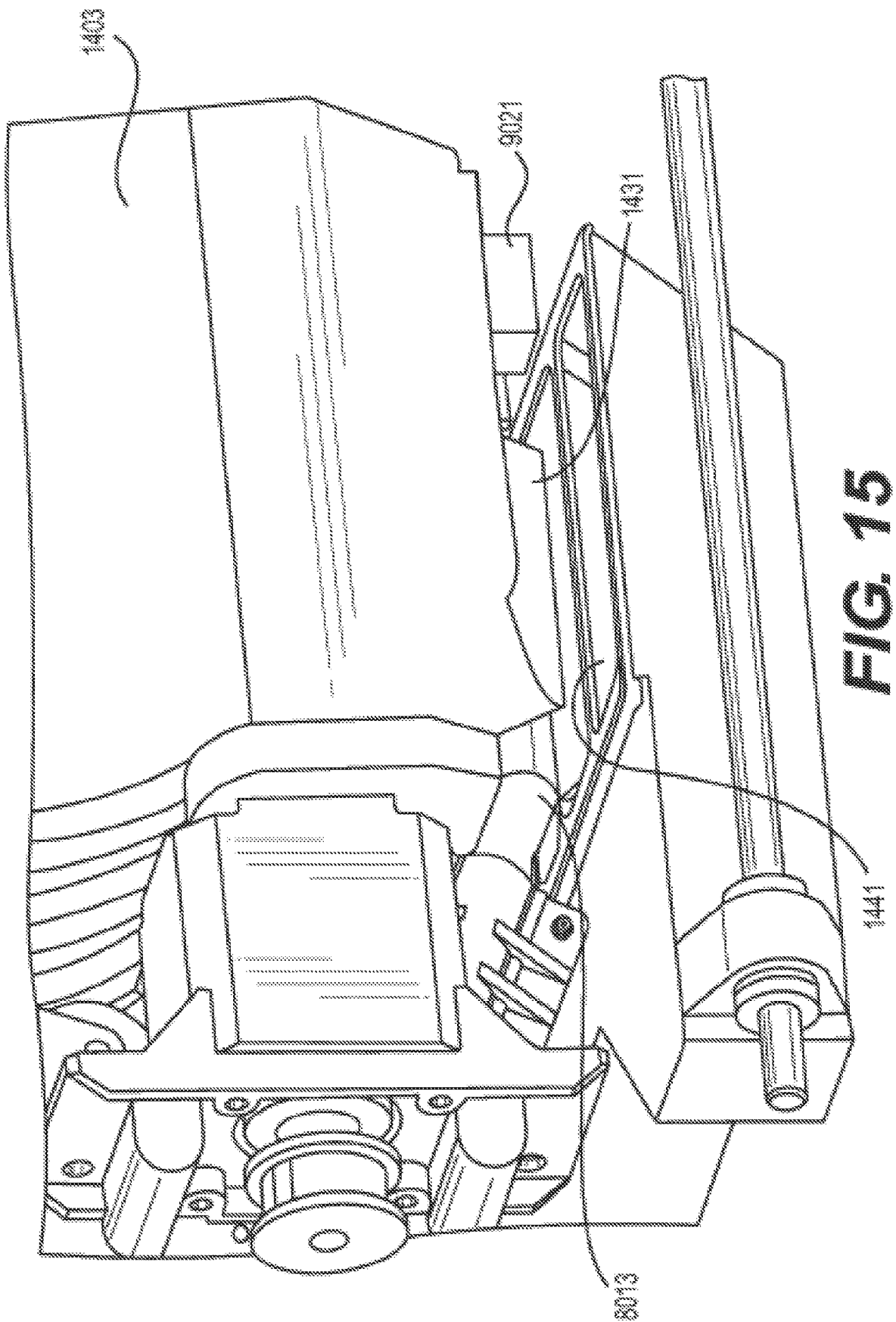
FIG. 15 illustrates the cartridge sensing elements in one embodiment of a patient-side device.

FIG. 15 illustrates the cartridge sensing elements 8013 in one embodiment of a patient-side device. This view may space between the cartridge 1403 sitting in the reservoir, and a tray positioned between the exit chute (not visible) of the cartridge 1403. Sensor 8013, which may be a camera or other device capable of identifying a pill in a tray, has a clear line of site into tray slot 1441. The sensor 8013 may scan the contents of slot 1441, and using one or more algorithms determine whether the contents of slot 1441 may be as expected (e.g., whether a pill was dispensed from the cartridge, and whether the dispensed pill may be the expected medication). In some embodiments, this pill verification may be automated, such that sensor 8013 may operate pursuant to one or more algorithms. In some embodiments, pill verification may be supplemented by an image capture for subsequent analysis by a medical professional or other third party. In some embodiments, the pill verification may also be performed live, such that a medical professional or other third party may receive the image or video footage from the patient-side device and confirm in or near real-time that the contents of slot 1441 may be correct.

As discussed above, cartridges 1403 may include an identifier 9021 with various information about the cartridge and its contents. In some embodiments, sensor 8013 may also read a portion of identifier 9021, to confirm the expected contents of the cartridge. Because multiple cartridges may be placed in near proximity, some embodiments may include a baffle 1431 on the reservoir, such that sensor 8013 may not inadvertently suffer from identifier crosstalk 9021 (e.g., receiving information from a neighboring cartridge's identifier).

Figure 16:
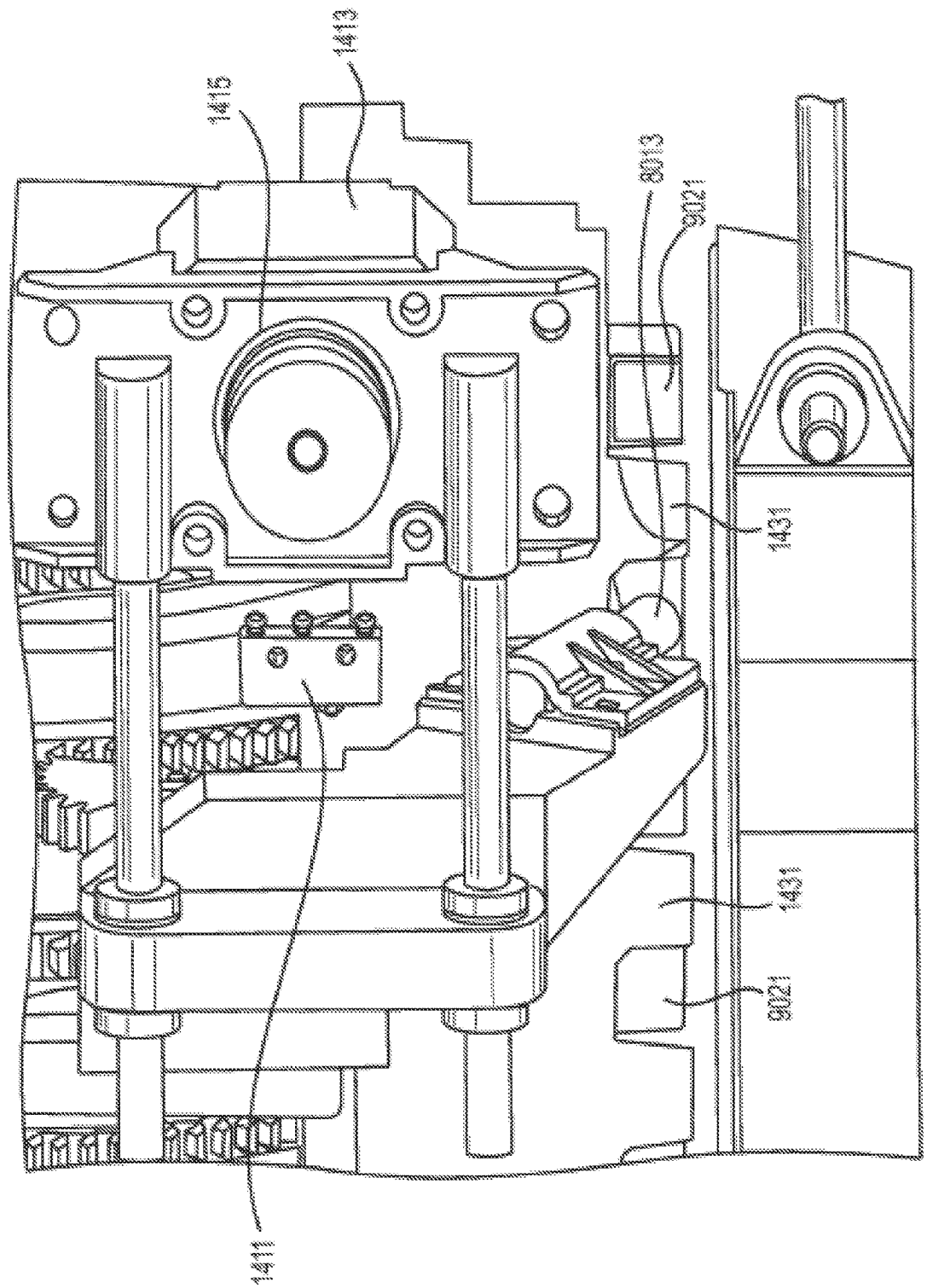
FIG. 16 shows another view of the cartridge sensing elements in one embodiment of a patient-side device.

FIG. 16 shows another view of the cartridge sensing elements in one embodiment of a patient-side device. In this view, the line of sight from indexing sensor 8013 may be visible. Additionally, the position of limit switch 1411 may be visible. In some embodiments, sensor 8013 may include an LED backlight, to assist in capturing an image or useful data relating to the dispensed contents and/or the cartridge.

Figure 17:
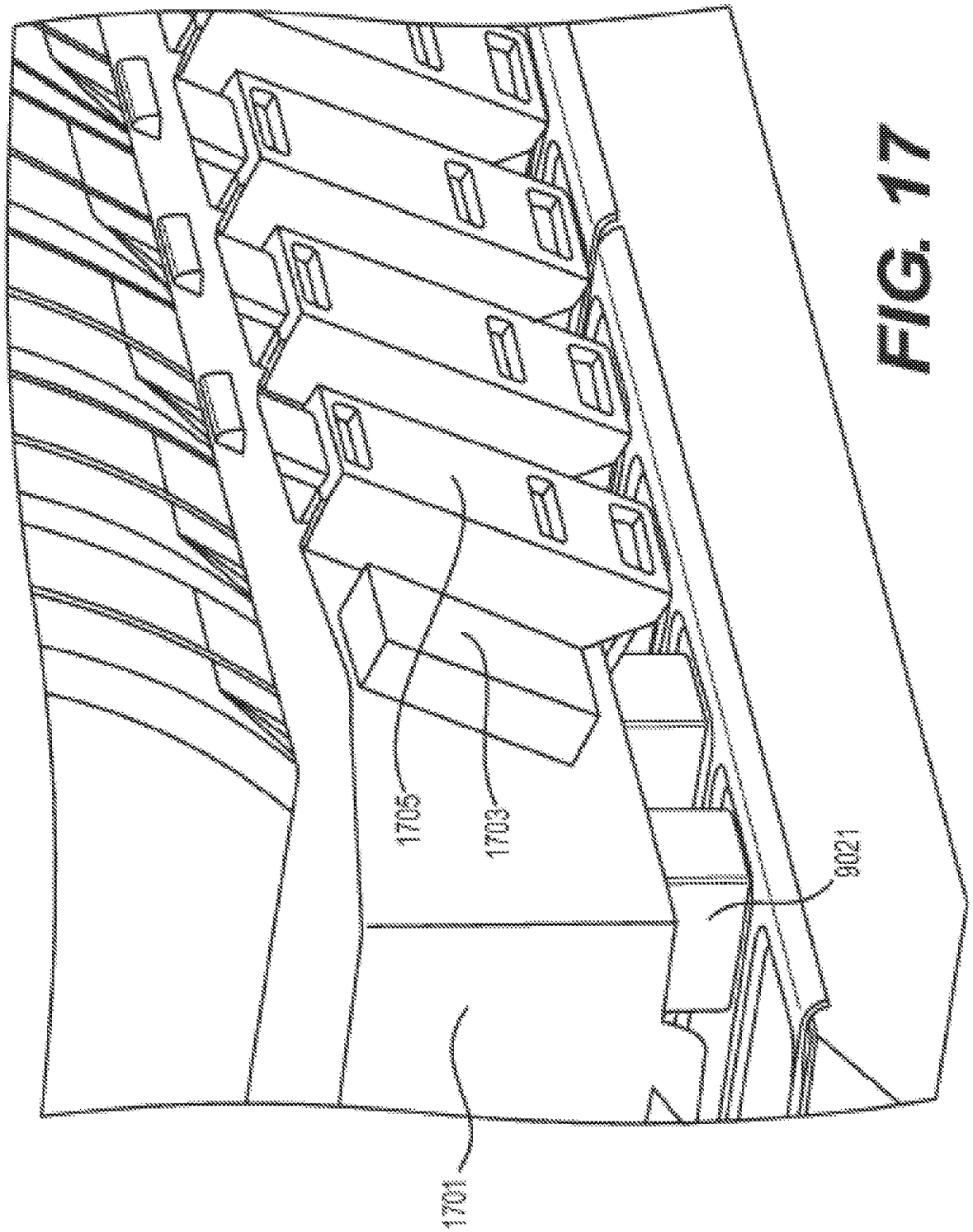
FIG. 17 depicts the cartridge tray according to one embodiment of the present approach.

A number of mechanisms may be used to securely position a cartridge in a reservoir. For example, force-fitting may be used, in which one or more detent members and corresponding structures allow the cartridge to 'snap' into the reservoir. FIG. 17 depicts the cartridge tray according to one embodiment of the present approach. Tray 1701 may include multiple reservoirs, and each reservoir may be configured to receive a cartridge. As discussed above, reservoirs may be configured to receive similar or dissimilar cartridges. A surface of tray 1701 may include a plurality of bar magnets 1703, such that one magnet 1703 may correspond to one reservoir slot for receiving a cartridge. When the cartridge may be inserted into the reservoir slot, magnet detention clips 1705 may be inserted to lock an individual cartridge in place.

Figure 18:
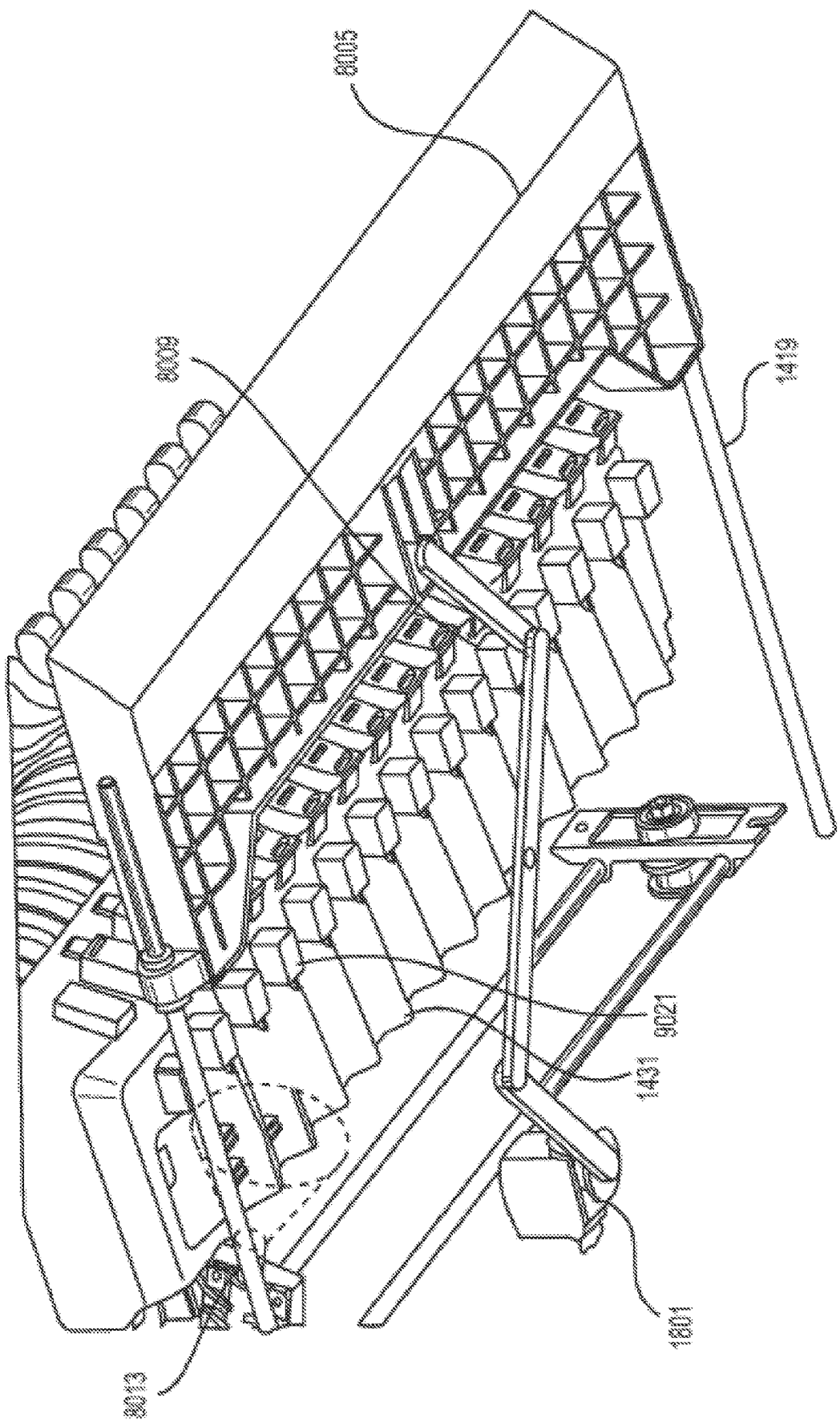
FIG. 18 shows the mechanical operation of the pill tray according to an embodiment of the present approach.

FIG. 18 shows the mechanical operation of the pill tray 8005 according to an embodiment of the present approach. Tray 8005 may extend outside of the device housing or retract inside the device housing along guide rods 1419. Extension mechanism 8009 may provide the mechanical force to extend and retract tray 8005. Motor 1801, which in this embodiment may be a high torque servo motor for precision control, may provide torque to the extension mechanism 8009. The torque may rotate one segment of the extension mechanism 8009 connected to the motor 1801. The displacement may cause a reciprocal extension or retraction of the opposing end of the extension mechanism connected to the tray 8005. In response, tray 8005 may move outward or inward along guide rods 1419. This view may also show the cone of the viewing angle for indexing sensor 8013.

Figure 19:
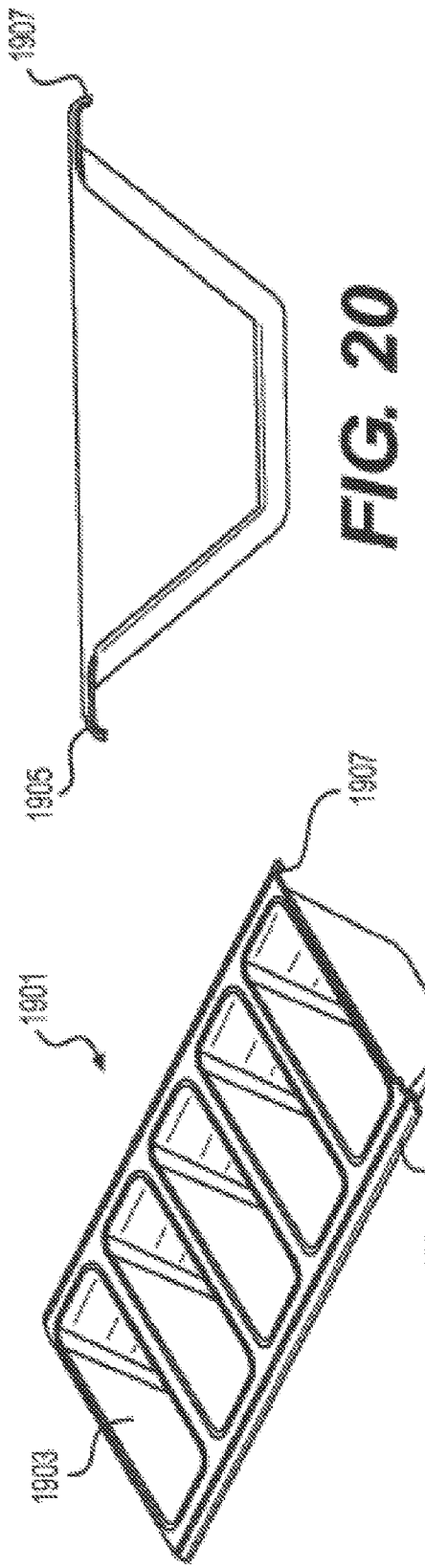
FIGS. 19-21 show perspective, side, and top views, respectively, of a pill tray, according to an embodiment of the present approach.
Figure 20:
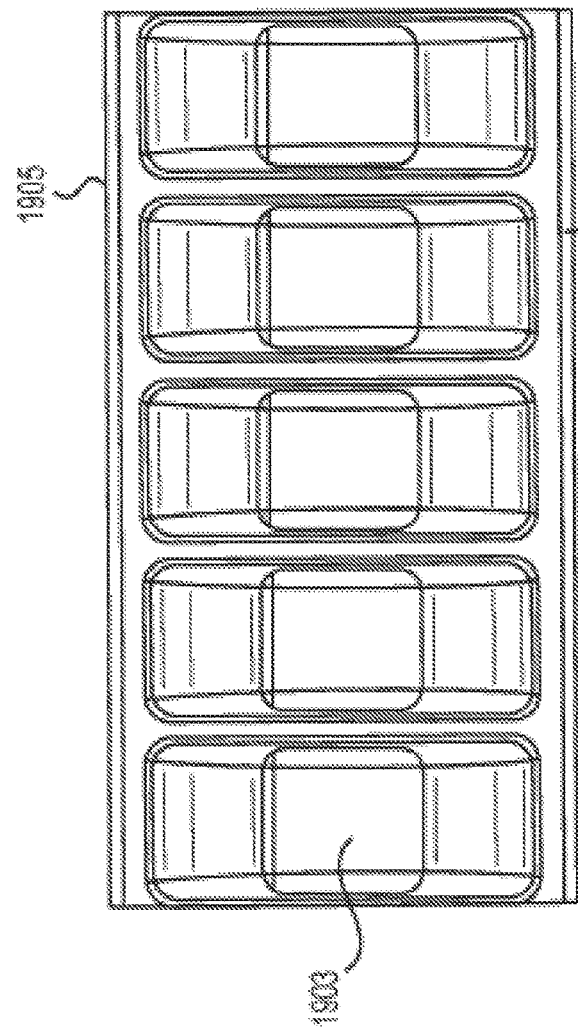
Figure 21:
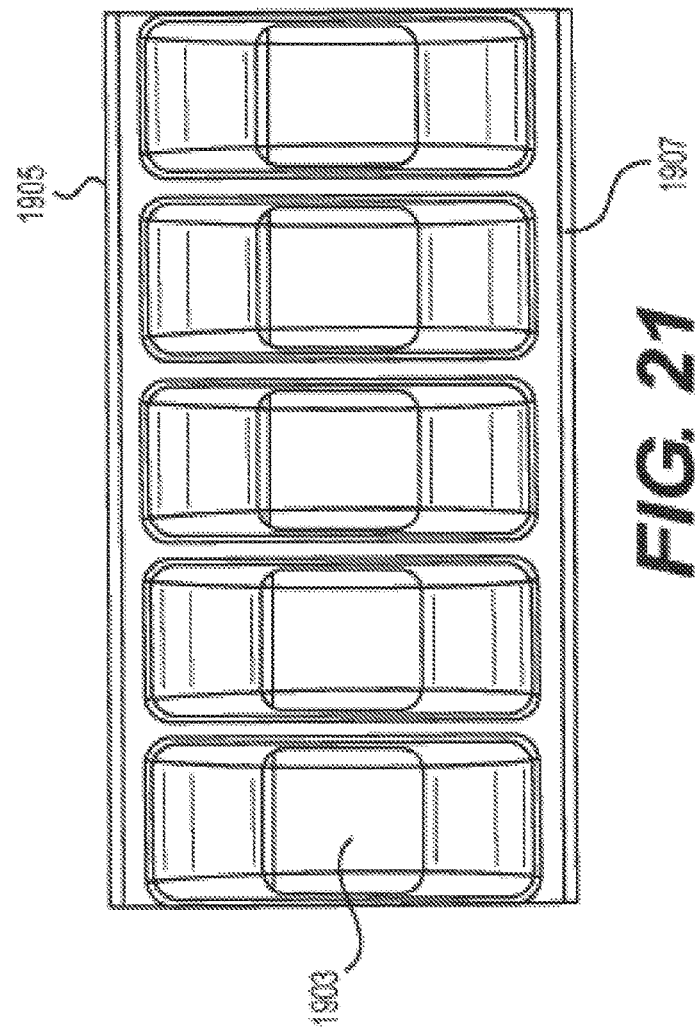

Some applications and pharmaceutical regulations may require disposable containers for dispensed medications. Embodiments of the present approach may feature removable and/or disposable pill trays. FIGS. 19-21 show perspective, side, and top views, respectively, of a pill tray 1901 according to an embodiment of the present approach. Pill tray 1901 may be remove-ably inserted into tray 8005, such that pill tray 1901 may be disposable. Ledges 1905 and 1907 may be used to secure pill tray 19 into tray 8005, such that pill tray 1901 may be unlikely to become dislodged during tray 8005 extension and jammed in the patient-side device. Each tray may include one or more slots 1903 for receiving dispensed pills. The shape of the slot 1903 may correspond with the shape of tray 8005. Slot 1903 may take a number of forms, depending on design preferences. As shown in FIG. 20, a slot 1903 may be trapezoidal, to conform with tray 8005 and also make it easier for a user to retrieve pill(s) dispensed into the slot 1903.

Computer Readable Medium

As will be appreciated by one of skill in the art, aspects or portions of the present approach may be embodied as a method, system, and/or process, and at least in part, on a computer readable medium. For example, the various algorithms for dispensing pills, measuring patient vital signs, identifying pills dispensed, communicating with and receiving instructions from medical professionals, and the like, may be embodied in a computer readable medium. The various algorithms may include machine learning algorithms. Machine learning algorithms may be used to train data sets to better dispensing pills, measuring patient's health status, identifying pills dispensed, communicating with and receiving instructions from medical professionals, and the like. The machine learning algorithms may comprise supervised learning algorithms, unsupervised learning algorithms, semi-supervised learning algorithms, reinforcement learning algorithms, deep learning algorithms, or any combination thereof. The machine learning algorithms may also comprise Support Vector Machine (SVM), Naïve Bayes (NB), Quadratic Discriminant Analysis (QDA), K-Nearest Neighbors (KNN), Linear Discriminant Analysis (LDA), and Multilayer Perceptron (MLP).

The computer readable medium may be used in connection with, or to control and/or operate, various pneumatic, mechanical, hydraulic, and/or fluidic elements used in systems, processes, and/or apparatus according to the present approach. Accordingly, the present approach may take the form of combination of apparatus, hardware and software embodiments (including firmware, resident software, microcode, etc.) or an embodiment combining software and hardware aspects that may all generally be referred to herein as a "circuit," "module" or "system." Furthermore, the present approach may include a computer program product on a computer readable medium having computer-usable program code embodied in the medium, and in particular control software. The present approach might also take the form of a combination of such a computer program product with one or more devices, such as a modular sensor brick, systems relating to communications, control, an integrate remote control component, etc.

Any suitable non-transient computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the non-transient computer-readable medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a device accessed via a network, such as the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any non-transient medium that can contain, store, communicate, propagate, or transport the program for use by or in connection with the instruction execution system, apparatus, or device.

Computer program code for carrying out operations of the present approach may be written in an object oriented programming language such as Java, C++, etc. However, the computer program code for carrying out operations of the present approach may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present approach may include computer program instructions that may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transient computer-readable memory, including a networked or cloud accessible memory, that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to specially configure it to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks. Any prompts associated with the present approach may be presented and responded to via a graphical user interface (GUI) presented on the display of the mobile communications device or the like. Prompts may also be audible, vibrating, etc.

Computer Control Systems

Figure 22:
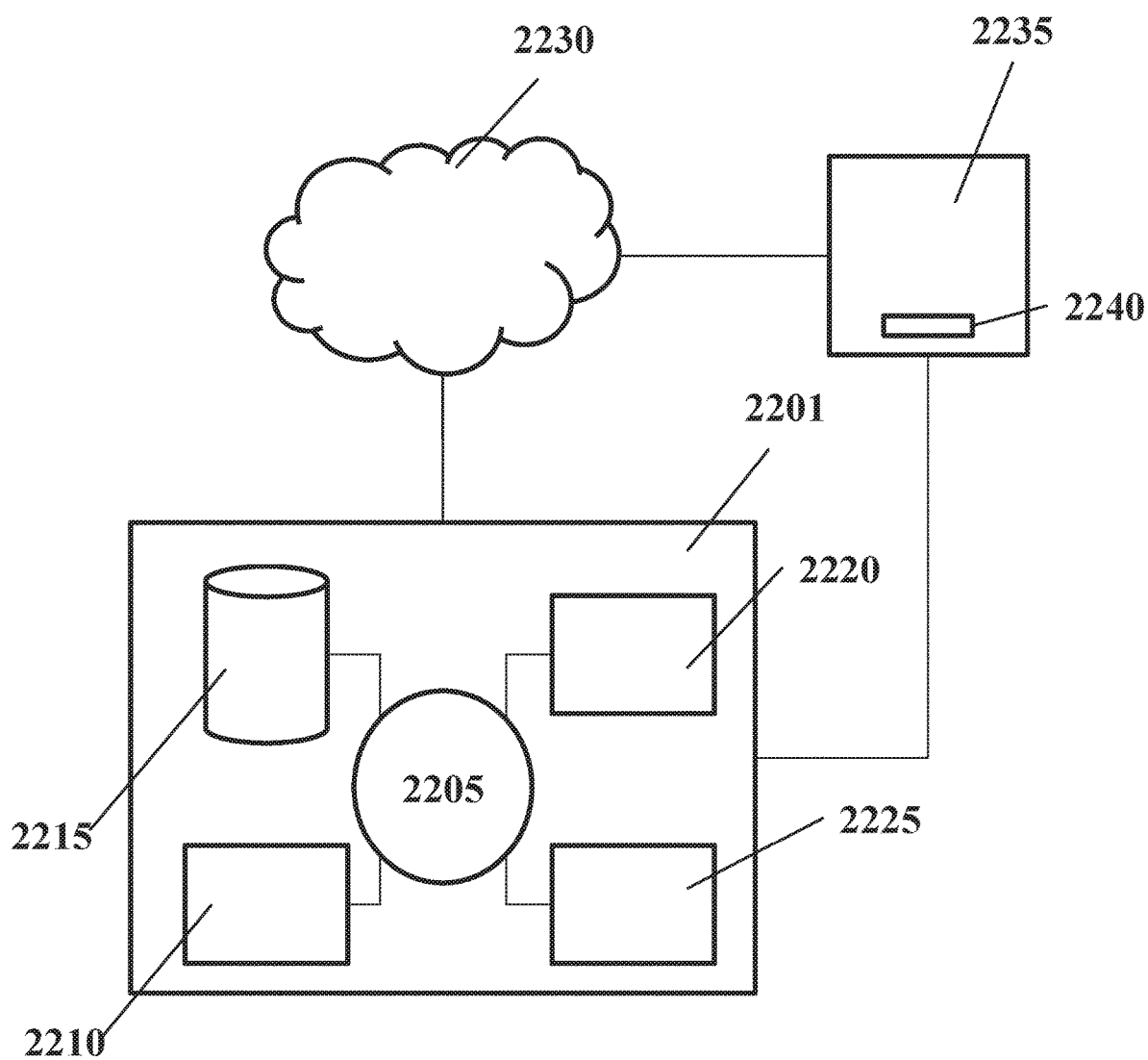
FIG. 22 shows a computer control system that is programmed or otherwise configured to implement methods provided herein.

The present disclosure provides computer control systems that are programmed to implement methods of the disclosure. FIG. 22 shows a computer system 2201 that is programmed or otherwise configured to control the patient-side health management device. The computer system 2201 can regulate various aspects of the present disclosure, such as, for example, storing data collected from the patient, sending signals to patient regarding the medication treatment schedule, and communicating from the patient to the medical professionals. The computer system 2201 can be an electronic device of a user or a computer system that is remotely located with respect to the electronic device. The electronic device can be a mobile electronic device.

The computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2230 with the aid of the communication interface 2220. The network 2230 can be the Internet, an internet and/or extranet, or an intranet and/or extranet that is in communication with the Internet. The network 2230 in some cases is a telecommunication and/or data network. The network 2230 can include one or more computer servers, which can enable distributed computing, such as cloud computing. The network 2230, in some cases with the aid of the computer system 2201, can implement a peer-to-peer network, which may enable devices coupled to the computer system 2201 to behave as a client or a server.

The CPU 2205 can execute a sequence of machine-readable instructions, which can be embodied in a program or software. The instructions may be stored in a memory location, such as the memory 2210. The instructions can be directed to the CPU 2205, which can subsequently program or otherwise configure the CPU 2205 to implement methods of the present disclosure. Examples of operations performed by the CPU 2205 can include fetch, decode, execute, and writeback.

The CPU 2205 can be part of a circuit, such as an integrated circuit. One or more other components of the system 2201 can be included in the circuit. In some cases, the circuit is an application specific integrated circuit (ASIC).

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user (e.g., mobile phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) 2240 for providing, for example, information regarding the medication, medication treatment schedule, exercise schedule, or health meal ideas. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2205. The algorithm can, for example, analyze data stored in the database and provide instructions to the patient.

MEASURING EMBODIMENTS

In some aspects, the device disclosed herein can be used to assess one or more pathology or suspected pathology or the effectiveness of a treatment of pathology described herein. Nail health may be assessed, analyzing convex curvature, i.e. the angle between the nail and the nail bed, and in addition to the other reports and/or information provided to the user, he may receive a graph of a degree of clubbing (normal, early, or late), based on nail bed shape and angle. Testicular health may be assessed according to a pain scale, new lumps, heaviness in scrotum region, and/or testicular swelling. Obstetric health may be assessed— weight, heart rate, blood pressure, portable ultrasound results, fetal heart rate assessment and analysis, and food intake, for example. Bone health may be assessed according to bone density, calcium level, activity level, pain scale, swelling, nutritional intake, and a bone densitometer score. Mental health may be determined by assessing speech recognition, level of consciousness (LOC), weakness on one side, blood pressure, visual changes, and/or NIH score. Ovulation health may be assessed by determining a surge in Luteinizing Hormone (LH) urine, analyzing cervical mucus consistency and/or basal body temperature (BBT). In addition to the other health information provided (raw data, graphs, charts, etc., ovulation results may include a digital calendar or listing of best ovulation times.

Spine health may be assessed according to structures or deformities, warmth, swelling, range of motion (ROM), presence of scoliosis, and gait. Joint health may be assessed by evaluating warmth to the area, ROM, swelling, presence of nodules, and/or gait. Skin health may be assessed according to skin turgor, color, skin breakdown, and degree of edema. Hair health may be assessed according to hair distribution, hair density, color, moisture content, dryness, texture, and presence of infection and/or infestation. Breast health may be determined based on swelling around the breast and armpit, pain level, changes to nipple, discharge, signs of lumps, and/or menstrual cycle issues. Information provided relative to breast health may additionally include a video showing a proper breast exam, and a digital model of the breast of the user or a hypothetical breast, again for examination purposes.

Foot health may be determined by collecting signs of infection, color, hair distribution, skin integrity, and degree of pitting or edema. In addition to the other reporting data, the system may provide a digital model of feet or the lower extremities. A general collection of parameters for the user may occur, including but not limited to collecting heart rate (HR), temperature (T), basal body temperature (BBT), respiratory rate (RR), SaO2, pulse oximetry, CO2, systolic blood pressure (SBP), diastolic blood pressure (DBP), urine chemistry, dry blood work, joint ROM, spine flexibility, muscle strength, BMI, total body water (as a percentage of body weight) in relation to age and sex, electrocardiogram (EKG), lung capacity (TV, TLC, VC, FRC, RV), height and weight, and body pH level. These and other pertinent values may be collected and reported and/or continuously tracked In the area of fitness and wellness, different module specific interactions may occur where data is received by the system or devices disclosed herein and certain information can be assessed and provided. In the area of fitness, the system may collect or receive user goals, weight loss values (current or desired), general fitness, preparation for an athletic event, muscle building, and rehabilitation from injury. Output may include an individualized fitness program as well as graphs and charts and recommendations. In the area of body building, height, weight, neck, chest, upper arm, waist, hips, and any other relevant area may be measured, and information about body fat provided as well as changes in body measurements. For sweat, the device may be provided with a module that analyzes user sweat and provides information on total free amino acids, ammonia, protein concentrations, and nitrogen balance of the user, detects a negative nitrogen balance, gives dietary recommendations, recommends post workout recovery meals, and recommends a dietary and supplement plan. For workout performance, the system or parts thereof may, analyze body mechanics during exercise by measuring weight distribution, relative angles at joints during exercise or body heat via thermal infrared camera. The device provides corrective user feedback on proper body mechanics during exercise. In the area of nutrition, the user may input daily food intake via picture, barcode scanner, or may select items consumed from a pull-down menu. Also provided or calculated are total calories, protein, carbohydrates, fat, and fiber. The system may recommend dietary changes toward fitness goals and may provide charts and graphs.

In the area of exercise, the system may collect or receive user submitted photos of gym equipment (at home or in gym), may enable interaction with a Personal Trainer, where the user communicates in real time with the Personal Trainer, time between sets, number of reps and weight lifted, body posture via angle of shoulders to waist and feet, and the system may recognize available equipment and build an exercise program. A trainer may observe the user while completing exercises and give real time feedback about technique. The system may provide motivational instruction. Recommendations by the Personal Trainer may optimize user exercise output. Physical health at work may be assessed by calculating angle of the body while seated and doing work, assuming the device or handheld unit is available at a representative workplace. The system may also calculate height of desk, chair, keyboard, and mouse. The system may recommend corrective body posture and ergonomic corrections to the work station. Physical health in the case of injury may be assessed, wherein a provider or the user or other appropriate individual may input the user's injury or injuries. The device may then create an exercise regimen based on the user's needs and specific injury.

In the wellness area of sleep architecture, the system may measure room temperature, amount of room light, noise, track user sleep/wake cycle, and the amount of movement during sleep. The system may recommend changes to sleep architecture. Tracks changes and saves users optimum sleep requirements. The system may also address menses, determining date of first day of the menstrual cycle, length of bleeding, bleeding volume, daily temperature, and may provide recommended dietary changes.

The system may also assess user demographic information, such as age, race, geographic location, profession, income, education, marital status, and number of children. From this, the system can determine a presentation specifically tailored to the user, determine style suggestions, price points, and clothing styles relating to seasons, temperatures, and precipitation, and allows retailers to focus on a specific consumer profile. The system may additionally determine clothing wear, possibly employing a sensor in user clothing, to determine date of wear, number of wearings, and frequency of wearings.

In the area of pharmaceuticals, the devices disclosed herein may make additional assessments or measurements and may determine recommendations and provide information to assist the user (subject or patent) in his or her personal care. One area can be prescription medications, wherein the system collects user name, quantity, dose, administration, duration of usage, refills, adverse reactions, use in specific populations, over dosage symptoms, over dosage signs, prescriber name, prescriber address, prescriber phone number, pharmacy name, pharmacy address, pharmacy phone number, controlled substance schedule (if applicable), price per unit, and medication expiration date. Certain information may be collected from third party sources if available, as is the case with other functions performed by the system. For example, if the medication is known, the system may submit a query seeking adverse reactions, or if a pharmacist is known, the system may seek the address and telephone number of the pharmacy from an online source. Information provided by the system may include a drug interactions alert, a refill alert, alternative medications options, generic medication options, an electronic update of current medication list to the device cloud, filling of the pill dispenser, lock filling into medication drawers if applicable, providing alternative price per unit information from other suppliers, an expiration date alert, and a next dose alert through cloud based system.

Over the counter supplements and supplies may also be assessed. Assessments may include name, quantity, dose, administration, duration of usage, refills, adverse reactions, use in specific populations, over dosage symptoms, over dosage signs, prescriber name, prescriber address, prescriber phone number, store name, store address, store phone number, price per unit, and/or expiration date. The information provided to the user may include a supplement interactions alert, a refill alert, alternative supplement options, an electronic update of current medication list, filling of a dispenser, alternative price per unit from other suppliers, and/or coupon options from suppliers.

The present design may be used in various scenarios, including but not limited to use of the design for pets or animals in addition to human personal care. In the pet scenario, the device may monitor a pet, such as a body temperature of a pet, using a module, and/or the location of a pet, such as using a collar with a GPS component or other position determining device.

The present design may further include an interactive diary function wherein the user can keep track of information and data related to his or her personal care and such information can be employed to better provide personal care for the user, either from an offsite location/central server device or from the device itself. The interactive diary can track pertinent parameters to the individual user in the area of personal care and wellness and may offer at least one recommendation. Interactive diaries for personal health and wellness may be offered in but not limited to the areas of health, fitness and sports, fashion, cosmetics, education, travel, finance, nutrition, pharmaceuticals, pets and/or horticulture. For example, the current design may monitor blood pressure and may track blood pressure. However, blood pressure is merely one data point in a plurality of data points related to an individual user, and when blood pressure is considered in connection with factors such as blood pressure readings over time, family history, weight, salt intake over time, smoking history, coffee intake over time, level of exercise, a more complete representation of the person may be determined. In such a situation, the individual may be encouraged to reduce coffee intake and/or exercise in a manner conducive to her ability. For example, if she has back issues, this may be known and encouragement to swim a certain amount per day three days per week might be recommended. A different person with a different profile but an identical blood pressure reading may be encouraged to decrease salt intake, reduce smoking, and to increase exercise by running two miles instead of 1.5 miles every day. The interactive diary function can encourage the user to provide more information and obtains a more complete profile of the individual. The present system may compile information using the interactive diary, either passively (without user input) or actively (e.g. by engaging the user, asking questions based on the action or situation presented), assesses the information generally by category, and makes recommendations or provides information to the user, or solicits additional specific information, in either general instances (e.g. displaying a target heart rate during exercise, displaying prior blood pressure readings when taking blood pressure) Such functionality may include progressing through logic trees or other logic progressions wherein information is assessed and suggestions or information provided for the benefit of the user.

In other embodiments, the device and systems disclosed herein can together or independently display or alert a subject visually or via an auditory feature of (1) the elapsed time since the last dose from a specific drawer was taken; (2) the time remaining until the next scheduled dose for a subject; (3) the number of times a specific drawer openings that have been recorded for that drawer in the current day, the last two intervals; (4) the number of pills to be taken in the next dose; (5) contra-indications; and/or (6) directions for taking the medication (e.g., take with food, water, etc.).

Language Support

A device provided herein can provide audible or visual messages in one or more languages, e.g., English, Spanish, French, Mandarin, Dutch, etc. In some embodiments, a device provided herein can support multiple languages including but not limited to German, English, French, Italian, Spanish, Polish, Portuguese, Swedish, Norwegian, Danish, Finnish, Lithuanian, Latvian, Estonian, Dutch, Greek, Catalan, Basque, Czech, Slovak, Arabic, Japanese, Chinese, Russian, Serbian, Croatian, Icelandic languages, Swahili, Bantu languages, Hindi and other languages of the world.

Biometric Sensor

In some embodiments, a biometric sensor can be a fingerprint sensor. Any type of fingerprint sensor known in the art can be used. In some embodiments, a fingerprint sensor can be a capacitive sensor. A capacitive sensor can use array capacitor plates to image a fingerprint. A sensor can measure capacitive coupling of skin of a fingertip as a subject or user's fingerprint is swiped or place over or on a fingerprint sensor. Because ridges of a fingertip can be closer to a detector when swiped, ridges can have a higher capacitance relative to valleys of a fingertip. In some embodiments, a capacitive sensor can apply a small voltage to a finger to enhance a signal and thereby provide a more accurate capacitive image of a fingertip.

In some embodiments, a fingerprint sensor can be an optical sensor. In such an embodiment, a detector can convert energy in light incidence on a detector into an electrical charge. In some embodiments, a detector can be a photodiode array detector. In other embodiments, a detector can be a phototransistor detector. In some embodiments, a sensor can comprise an LED to illuminate a finger and thereby provide a more accurate optical image of a fingertip. In some embodiments, an optical sensor can be a charge-coupled-device based optical imager. In other embodiments, an optical sensor can be a complementary metal-oxide-semiconductor (CMOS)-based optical imager. In some embodiments, a fingerprint sensor can be a thermal sensor. In some embodiments, an individual's finger can be placed on a sensor, where a sensor can comprise a pyro-electric material. A pyro-electric material can then measure a contact temperature of a finger. Ridges of a finger, which can make contact with a pyro-electric material, can be imaged while valleys, which in some cases do not make contact with a pyro-electric material, may not be imaged. A temperature differential between ridges and valleys of a fingertip can be used to create a thermal image of the fingertip.

In some embodiments, a fingerprint sensor can be a pressure sensor. In such an embodiment, a fingerprint can be imaged through physical contact of an individual's fingertip with a thin film in which a physical impression of a fingertip can be recorded. In some embodiments, a pressure sensor can be a conductive film detector. In some embodiments, a sensor can comprise a double-layer electrode on flexible films. In some embodiments, a pressure sensor can be a micro-electro-mechanical device. In some embodiments, a sensor can comprise tiny silicon switches on a silicon chip such that when a fingerprint ridge touches a switch, a switch closes and a ridge can be detected electronically.

In some embodiments, a fingerprint sensor can be a radio frequency (RF) sensor. A low frequency RF signal can be applied to an individual's fingertip. A signal can then be read by a detector array, with each pixel operating like a tiny antenna. This detector array can then be used to provide an image of a fingertip contours pixel by pixel. In some embodiments, a fingerprint sensor can be an ultrasonic sensor. In some embodiments, a sensor uses sound waves to penetrate a surface layer of a skin, which can provide a 3 dimensional image of an individual's fingerprint from the inside out. In some embodiments, an ultrasonic sensor can comprise steel, sapphire, glass or plastic. In some embodiments, any of the fingerprint sensors described above can be employed as a static fingerprint sensor. In some embodiments, an individual's finger can be placed motionless on a surface prior to collecting an image. In other embodiments, any of the fingerprint sensors described above can be employed as a swipe fingerprint reader, in which an individual's finger can be dragged across a sensor, and a complete image can be put together by appending partial images of a finger together.

In some embodiments, a biometric sensor can be a retinal scanner. In some embodiments, a biometric sensor can be a facial recognition scanner. In some embodiments, a retinal scanner can comprise a small camera used to capture images of an individual's retina. In some embodiments, a retinal scanner can comprise an infrared light source used to illuminate a retina. In some embodiments, an individual can position his or her eye proximal to a lens of a retinal sensor prior to use. In some embodiments, an infrared light can illuminate an individual's retina, and a camera can then scan a retina of an individual. A sensor can capture and analyze patterns of blood vessels on a thin nerve on a back of an eyeball that processes light. This pattern of blood vessels can be unique among individuals, allowing for accurate identification of an individual.

In some embodiments, a biometric sensor can be a voice recognition sensor. A voice recognition sensor can comprise a microphone capable of recording and analyzing an individual's voice. A digital profile of an individual's voice can be recorded by having an individual speak. A spoken word can then be converted into segments composed of several dominant frequencies, which can be used to construct a digital profile of an individual's voice. In some embodiments, an individual can be instructed to recite an alphabet. In other embodiments, an individual can be instructed to recite a series of numbers. In other embodiments, an individual can be instructed to recite a predetermined series of words. In other embodiments, an individual can be given a unique password to recite, which can be used in subsequent authentication sessions to positively identify an individual.

In other embodiments, a biometric reader can be a biometric sensor. A biometric sensor can be one or more of a temperature sensor, a galvanic skin response sensor, a pulse oximeter, a carbon dioxide sensor, an oxygen sensor, an optical sensor, an air flow velocity sensor, an air pressure sensor, a chemical sensor, and a global positioning system (GPS) sensor or other known sensor.

In other embodiments, a device described herein can comprise a processor comprising one or more software programs for operating the at least one biometric sensor and for facilitating the acquisition of biometric data using the at least one biometric sensor.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

EXAMPLES

These examples are provided for illustrative purposes only and not to limit the scope of the claims provided herein.

Example 1: Vital Signs Measurements are Outside Ranges

The patient-side device may allow medical professionals to customize vital sign ranges on the device, even when the medical professionals are not on site. In the illustrated example, the patient-side device is placed in an apartment, house, or an area wherein a subject is present. The patient-side device is connected to a medical professional-side device through internet. A medical professional obtains patient's medical history though a centralized database. The medical professional also communicates with the patient using his/her medical professional-side device to ask patient questions related his/her health. The medical professional asks, for instance, "how do you feel today," "did you take any vitamins," "did you smoke." The patient answers these questions by using the patient-side device. In this example, the communication is conducted through video. After the medical professional gathers relevant information, he/she enters the numbers of the customized vital sign ranges and sends the ranges to the patient-side device. In the illustrated example, the medical professional sets up the range of body temperature from 97 degrees Fahrenheit to 99 degrees Fahrenheit, the range of the respiration rate as from 12 to 16 breaths per minute, the range of the pulse rate as from 60 to 100 beats per minute, and the rage of blood pressure as less than 120 for systolic and less than 80 for diastolic. The patient then chooses to accept the customized vital sign ranges on the patient-side device.

The patient-side device is connected with one or more apparatus to measure the patient's vital signs. The one or more apparatus include a thermometer, stop watch, sphygmomanometer, and stethoscope. The patient measures his/her vital signs once per day. On certain day, the patient's body temperature is 100 degrees Fahrenheit. In this situation, the patient-side device sends an alert to the medical professional-side device. The alert can be a message, an alarm (visual or auditory). The medical professional reads the alert and starts communication with the patient. The communication is conducted through video. After the communication, the medical professional sends updated prescription to the patient-side device. The updated prescription instructs the patient to take certain medications in order to lower the patient's body temperature.

Example 2: the Patient-Side Device Alerts the Patient to Come to the Device in a Residence The patient-side device is placed in a study room in a single family house of a patient. The patient-side device is connected and communicates with a Fitbit worn by the patient. The patient is scheduled to take vitamins at 6:00 pm every day. At 6:05 pm, the patient forgets to take the vitamins. The patient is in the kitchen to cook dinner. The patient-side device sends an alert signal to the Fitbit worn by the patient. The speaker on the Fitbit worn by the patient is triggered and starts to produce alarm, which notifies the patient that he/she forgets to take vitamins. The patient then enters into the study room and goes to the patient-side device to obtain the vitamins.

Example 3: the Patient-Side Device is Placed on the Plane

The patient-side device is dimensioned to fit the isle of an airplane. The patient-side device comprises one or more apparatus to check a patient's health status and/or measure the patient's physical conditions. The one or more apparatus include a thermometer, stop watch, sphygmomanometer, and stethoscope. The apparatus are portable and operatively coupled with the patient-side device. The patient-side device holds 70 medications that are normally used by the public.

In the illustrated example, a passenger on the plane does not feel comfortable and asks the flight attendant's help. In this situation, the flight attendant rolls the patient-side device to the passenger. The patient-side device then enables a communication between the passenger and a medical professional who is not on the plane. The communication is conducted through a wireless connection. The communication is in the form of video. The medical professional asks the passenger questions related to the passenger's health, such as, for example, passenger's age, height, weight, BMI, blood pressure, resting pulse, medical history, mental health status, sex, race, ethnicity, diet, or other risk factors such as smoking, and drug or alcohol abuse. The medical professional also asks the flight attendant to help check the patient's health status by using the apparatus. After obtaining enough information, the medical professional provides instructions to the flight attendant to give certain medications to the passenger. The medical professional also informs the patient to take a rest and drink more water. The flight attendant then gains access to the patient-side device to take out the medication prescribed by the medical professional and give the medication to the passenger.

Example 4: the Patient-Side Device is Placed in a School

The patient-side device is dimensioned to be placed in a hall way of a building in a school. The patient-side device comprises one or more apparatus to check the patient's health status and/or measure the patient's physical conditions. The one or more apparatus include a thermometer, stop watch, sphygmomanometer, and stethoscope. The apparatus are portable and operatively coupled with the patient-side device. The patient-side device holds 200 medications.

In the illustrated example, a student in the school does not feel comfortable during a class and he/she leaves the classroom to use the patient-side device in the hall way. The patient-side device then enables a communication between the student and a medical professional who is not onsite. The communication is conducted through a wireless connection. The communication is in the form of video. The medical professional asks the student questions related to the student's health, such as, for example, the student's age, height, weight, BMI, blood pressure, resting pulse, medical history, mental health status, sex, race, ethnicity, diet, or other risk factors such as smoking, and drug or alcohol abuse. The medical professional also asks the student to check his/her health status by using the apparatus. After obtaining enough information, the medical professional provides instructions to the student about which medication to take and the dosage of the medication. The student then opens a drawer on the patient-side device assigned to him/her and obtain the medication prescribed by the medical professional.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A patient-side medical device comprising:
   a. a dispensing area comprising a plurality of drawers adapted to receive or dispense one or more medications, wherein the plurality of drawers is configured to allow dispensing to be remotely controlled or monitored by a medical professional;
   b. a rotating wheel mechanism configured to funnel the one or more medications by gravity from the rotating wheel mechanism via a chute;
   c. a verification area configured to receive the one or more medications after the one or more medications is dropped from the chute and before the one or more medications can move into the dispensing area;
      wherein the verification area comprises a camera sensor configured to verify the identity of the one or more medications based on an image of the one or more medications, wherein the verification area is configured to verify the one or more medications prior to allowing the one or more medications to travel to the dispensing area;
      wherein the camera sensor is embedded within and operably coupled to the patient-side medical device; and
      wherein the camera sensor is controlled by a processor natively embedded in the patient-side medical device;
   d. at least one visual display, wherein at least one of the at least one visual display is configured to allow communication with the medical professional;
   e. at least one biometric sensor for acquiring biometric data of a subject; and
   f. a processor configured to change, based at least in part on a patient vital sign measurement changing over time:
      i. a medication dispensing schedule;
      ii. the one or more medications; or
      iii. a dosage of the one or more medications,
      wherein the patient-side medical device is configured to collect the patient vital sign measurement over time.

2. The patient-side medical device of claim 1, wherein the at least one biometric sensor is a fingerprint reader, a retinal scanner, or a facial recognition reader.

3. The patient-side medical device of claim 1, wherein the at least one biometric sensor is a fingerprint reader.

4. The patient-side medical device of claim 1, wherein the biometric data is acquired prior to dispensing the one or more medications to the subject.

5. The patient-side medical device of claim 1, wherein the biometric data authenticates the subject.

6. The patient-side medical device of claim 1, wherein the patient-side medical device does not dispense the one or more medications to the subject prior to authenticating the subject.

7. The patient-side medical device of claim 1, wherein the patient-side medical device is in communication with a peripheral device.

8. The patient-side medical device of claim 7, wherein the communication comprises wireless communication.

9. The patient-side medical device of claim 7, wherein the peripheral device comprises a global positioning system (GPS), a blood pressure monitor, a blood glucose monitor, a CPAP machine, an electrocardiogram device, a spirometer, a pulse oximeter, a digital scale, a thermometer, or any combination thereof.

10. The patient-side medical device of claim 7, wherein the patient vital sign measurement is generated by the peripheral device.

11. The patient-side medical device of claim 10, wherein the patient vital sign measurement is a blood pressure measurement of the subject.

12. The patient-side medical device of claim 10, wherein the patient vital sign measurement is a blood glucose level of the subject.

13. The patient-side medical device of claim 10, wherein the patient vital sign measurement is a blood oxygen level of the subject.

14. The patient-side medical device of claim 10, wherein the patient vital sign measurement is a sinus rhythm of the subject.

15. The patient-side medical device of claim 14, wherein the sinus rhythm is a normal sinus rhythm, a sinus tachycardia, a sinus bradycardia, an atrial fibrillation, an atrial flutter, a ventricular tachycardia, or a ventricular fibrillation.

16. The patient-side medical device of claim 1, wherein the patient vital sign measurement is stored on the patient-side medical device.

17. The patient-side medical device of claim 1, wherein the patient vital sign measurement is transmitted to a database or server.

18. The patient-side medical device of claim 1, wherein the patient vital sign measurement is compared to a reference.

19. The patient-side medical device of claim 1, wherein the patient-side medical device is configured to be stored in a transportation system.

20. The patient-side medical device of claim 1, wherein the medical professional is a treating physician, a registered nurse, or a combination thereof.

21. The patient-side medical device of claim 20, wherein the medical professional is operating a computing device in communication with the patient-side medical device.

22. The patient-side medical device of claim 1, wherein the patient vital sign measurement comprises a measurement of a body temperature, a pulse rate, a respiration rate, a blood pressure, a blood oxygen level, a blood glucose level, a patient's weight, a patient's BMI, or any combination thereof.

23. The patient-side medical device of claim 22, wherein the processor is configured to change based at least in part on the patient vital sign being measured to be outside a range specified by the medical professional.

24. The patient-side medical device of claim 23, wherein the patient-side medical device is configured to collect patient vital sign data from a patient at least once every day.

25. The patient-side medical device of claim 1, wherein the patient-side medical device comprises a hub for collecting the patient vital sign data.

26. The patient-side medical device of claim 1, further comprising a pill reservoir configured to hold a plurality of pill cartridges.

27. The patient-side medical device of claim 26, wherein at least one pill cartridge in the plurality of pill cartridges comprises an identifier on the at least one pill cartridge.

28. The patient-side medical device of claim 27, further comprising a sensor configured to verify the one or more medications to be dispensed from the at least one pill cartridge by sensing the identifier on the at least one pill cartridge.

29. The patient-side medical device of claim 28, wherein the one or more medications comprises a capsule, a tablet, a juice, a powder, a suspension, an emulsifier, a granule, a troch, a pill, a spirit, or a syrup.

30. The patient-side medical device of claim 28, wherein the identifier is a barcode, and the sensor is a barcode reader.

31. The patient-side medical device of claim 1, wherein the rotating wheel mechanism comprises a slot through which the one or more medications is funneled by gravity into the chute.

32. The patient-side medical device of claim 31, wherein the chute is beneath the rotating wheel mechanism.

33. The patient-side medical device of claim 1, wherein the patient-side medical device is configured to capture an image of the one or more medications using the camera sensor.

34. The patient-side medical device of claim 33, wherein the patient-side medical device is configured to transmit the image of the one or more medications to the medical professional or a third party.

35. The patient-side medical device of claim 1, wherein the patient-side medical device further comprises an automated visual recognition module that is configured to identify the one or more medications by appearance using the camera sensor.

36. The patient-side medical device of claim 1, wherein the camera sensor is an optical detection apparatus configured to optically read or scan a visual element.

37. The patient-side medical device of claim 1, wherein the rotating wheel mechanism is a vertical rotating wheel mechanism.

38. The patient-side medical device of claim 1, further comprising a plurality of pill reservoirs configured to hold a plurality of medications.

39. The patient-side medical device of claim 1, wherein the patient-side medical device is configured to automatically verify the medication.

40. The patient-side medical device of claim 1, further comprising an array of pill reservoirs configured to hold the one or more medications or a plurality of pill cartridges.

41. The patient-side medical device of claim 1, wherein the camera sensor is configured to track the one or more medications as the one or more medications leaves a pill cartridge and travels to the verification area or dispensing area.

* * * * *